United States Patent
Hock et al.

(10) Patent No.: US 7,193,051 B2
(45) Date of Patent: Mar. 20, 2007

(54) HISTIDINE PHOSPHATASE INTERACTING PROTEIN WITH 240KD

(75) Inventors: Bjoern Hock, Maintal (DE); Klaus Duecker, Darmstadt (DE); Roland Kellner, Heppenheim (DE)

(73) Assignee: Merck Patent GmbH, Darmstadt (DE)

( * ) Notice: Subject to any disclaimer, the term of this patent is extended or adjusted under 35 U.S.C. 154(b) by 439 days.

(21) Appl. No.: 10/468,027

(22) PCT Filed: Jan. 30, 2002

(86) PCT No.: PCT/EP02/00917

§ 371 (c)(1),
(2), (4) Date: Aug. 14, 2003

(87) PCT Pub. No.: WO02/074796

PCT Pub. Date: Sep. 26, 2002

(65) Prior Publication Data

US 2004/0143102 A1    Jul. 22, 2004

(30) Foreign Application Priority Data

Feb. 16, 2001   (EP)   ................... 01103780

(51) Int. Cl.
*C07K 1/00*      (2006.01)
*C07K 16/00*     (2006.01)
*C07H 21/04*     (2006.01)
*C12Q 1/00*      (2006.01)

(52) U.S. Cl. .................. 530/350; 435/4; 536/23.4; 530/387.9

(58) Field of Classification Search ............... 435/4, 435/23.4; 530/350, 387.9
See application file for complete search history.

(56) References Cited

FOREIGN PATENT DOCUMENTS

| WO | WO 0170808 | 9/2001 |
|---|---|---|
| WO | WO 02070676 | 9/2002 |

OTHER PUBLICATIONS

Database NCBI 'Online!, Kikuno et al., "Homo sapiens mRNA for KIAA1058 protein, partial cds," retrieved from EBI, accession No. AB028981, XP002215235, the whole document; & Kikuno et al., "Prediction of the coding sequences of unidentified human genes. XIV. The complete sequence of 100 new cDNA clones from brain which code for large proteins in vitro," DNA Research, 1999, pp. 197-205, vol. 6, XP000852618, tables 1 and 2, fig. 1.
Kim Younhee et al., "Protein phosphatases 1, 2A, and 2C are protein histidine phosphatases," Journal of Biological Chemistry, 1993, pp. 18513-18518, vol. 268, No. 25, XP002215233, ISSN: 0021-9258, the whole document.

*Primary Examiner*—Rebecca E. Prouty
*Assistant Examiner*—Iqbal Chowdhury
(74) *Attorney, Agent, or Firm*—Millen, White, Zelano, Branigan, P.C.

(57) ABSTRACT

PHPIP-240 polypeptides and polynucleotides and methods for producing such polypeptides by recombinant techniques are disclosed. Also disclosed are methods for utilizing PHPIP-240 polypeptides and polynucleotides in diagnostic assays.

4 Claims, No Drawings

SEQUENCE LISTING

<160> NUMBER OF SEQ ID NOS: 9

<210> SEQ ID NO 1
<211> LENGTH: 7500
<212> TYPE: DNA
<213> ORGANISM: Homo sapiens
<220> FEATURE:
<221> NAME/KEY: CDS
<222> LOCATION: (43)..(6366)

<400> SEQUENCE: 1

| | | |
|---|---|---|
| gccgcgggag caggcggagg cggaggcggc gggggcagga gg atg tcg cag ccg<br>                                                                                                     Met Ser Gln Pro<br>                                                                                                     1 | 54 |
| ccg ctg ctc ccc gcc tcg gcg gag act cgg aag ttc acc cgg gcg ctg<br>Pro Leu Leu Pro Ala Ser Ala Glu Thr Arg Lys Phe Thr Arg Ala Leu<br> 5                         10                    15                    20 | 102 |
| agt aag ccg ggc acg gcg gcc gag ctg cgg cag agc gtg tct gag gtg<br>Ser Lys Pro Gly Thr Ala Ala Glu Leu Arg Gln Ser Val Ser Glu Val<br>                      25                    30                    35 | 150 |
| gtg cgc ggc tcc gtg ctc ctg gca aag cca aag cta att gag cca ctc<br>Val Arg Gly Ser Val Leu Leu Ala Lys Pro Lys Leu Ile Glu Pro Leu<br>             40                    45                    50 | 198 |
| gac tat gaa aat gtc atc gtc cag aag aag act cag atc ctg aac gac<br>Asp Tyr Glu Asn Val Ile Val Gln Lys Lys Thr Gln Ile Leu Asn Asp<br>        55                    60                    65 | 246 |
| tgt tta cgg gag atg ctg ctc ttc cct tac gat gac ttt cag acg gcc<br>Cys Leu Arg Glu Met Leu Leu Phe Pro Tyr Asp Asp Phe Gln Thr Ala<br> 70                          75                    80 | 294 |
| atc ctg aga cga cag ggt cga tac ata tgc tca aca gtg cct gcg aag<br>Ile Leu Arg Arg Gln Gly Arg Tyr Ile Cys Ser Thr Val Pro Ala Lys<br> 85                          90                    95                  100 | 342 |
| gcg gaa gag gaa gca cag agc ttg ttt gtt aca gag tgc atc aaa acc<br>Ala Glu Glu Glu Ala Gln Ser Leu Phe Val Thr Glu Cys Ile Lys Thr<br>                      105                  110                  115 | 390 |
| tat aac tct gac tgg cat ctt gtg aac tat aaa tat gaa gat tac tca<br>Tyr Asn Ser Asp Trp His Leu Val Asn Tyr Lys Tyr Glu Asp Tyr Ser<br>             120                    125                  130 | 438 |
| gga gag ttt cga cag ctt ccg aac aaa gtg gtc aag ttg gat aaa ctt<br>Gly Glu Phe Arg Gln Leu Pro Asn Lys Val Val Lys Leu Asp Lys Leu<br>             135                    140                  145 | 486 |
| cca gtt cat gtc tat gaa gtt gac gag gag gtc gac aaa gat gag gat<br>Pro Val His Val Tyr Glu Val Asp Glu Glu Val Asp Lys Asp Glu Asp<br>150                    155                    160 | 534 |
| gct gcc tcc ctt ggt tcc cag aag ggt ggg atc acc aag cat ggc tgg<br>Ala Ala Ser Leu Gly Ser Gln Lys Gly Gly Ile Thr Lys His Gly Trp<br>165                    170                    175                  180 | 582 |
| ctg tac aaa ggc aac atg aac agt gcc atc agc gtg acc atg agg tca<br>Leu Tyr Lys Gly Asn Met Asn Ser Ala Ile Ser Val Thr Met Arg Ser<br>                      185                  190                  195 | 630 |
| ttt aag aga cga ttt ttc cac ctg att caa ctt ggc gat gga tcc tat<br>Phe Lys Arg Arg Phe Phe His Leu Ile Gln Leu Gly Asp Gly Ser Tyr<br>             200                    205                  210 | 678 |
| aat ttg aat ttt tat aaa gat gaa aag atc tcc aaa gaa cca aaa gga<br>Asn Leu Asn Phe Tyr Lys Asp Glu Lys Ile Ser Lys Glu Pro Lys Gly<br>             215                    220                  225 | 726 |
| tca ata ttt ctg gat tcc tgt atg ggt gtc gtt cag aac aac aaa gtc<br>Ser Ile Phe Leu Asp Ser Cys Met Gly Val Val Gln Asn Asn Lys Val<br>             230                    235                  240 | 774 |
| agg cgt ttt gct ttt gag ctc aag atg cag gac aaa agt agt tat ctc<br>Arg Arg Phe Ala Phe Glu Leu Lys Met Gln Asp Lys Ser Ser Tyr Leu<br>245                    250                    255                  260 | 822 |
| ttg gca gca gac agt gaa gtg gaa atg gaa gaa tgg atc aca att cta<br>Leu Ala Ala Asp Ser Glu Val Glu Met Glu Glu Trp Ile Thr Ile Leu<br>                      265                  270                  275 | 870 |
| aat aag atc ctc cag ctc aac ttt gaa gct gca atg caa gaa aag cga<br>Asn Lys Ile Leu Gln Leu Asn Phe Glu Ala Ala Met Gln Glu Lys Arg<br>             280                    285                  290 | 918 |

```
                                                    -continued aat ggc gac tct cac gaa gat gat gaa caa agc aaa ttg gaa ggt tct       966
Asn Gly Asp Ser His Glu Asp Asp Glu Gln Ser Lys Leu Glu Gly Ser
            295                 300                 305 ggt tcc ggt tta gat agc tac ctg ccg gaa ctt gcc aag agt gca aga      1014
Gly Ser Gly Leu Asp Ser Tyr Leu Pro Glu Leu Ala Lys Ser Ala Arg
310                 315                 320 gaa gca gaa atc aaa ctg aaa agt gaa agc aga gtc aaa ctt ttt tat      1062
Glu Ala Glu Ile Lys Leu Lys Ser Glu Ser Arg Val Lys Leu Phe Tyr
325                 330                 335                 340 ttg gac cca gat gcc cag aag ctt gac ttc tca tca gct gag cca gaa      1110
Leu Asp Pro Asp Ala Gln Lys Leu Asp Phe Ser Ser Ala Glu Pro Glu
                345                 350                 355 gtg aag tca ttt gaa gag aag ttt gga aaa agg atc ctt gtc aag tgc      1158
Val Lys Ser Phe Glu Glu Lys Phe Gly Lys Arg Ile Leu Val Lys Cys
            360                 365                 370 aat gat tta tct ttc aat ttg caa tgc tgt gtt gcc gaa aat gaa gaa      1206
Asn Asp Leu Ser Phe Asn Leu Gln Cys Cys Val Ala Glu Asn Glu Glu
        375                 380                 385 gga ccc act aca aat gtt gaa cct ttc ttt gtt act cta tcc ctg ttt      1254
Gly Pro Thr Thr Asn Val Glu Pro Phe Phe Val Thr Leu Ser Leu Phe
390                 395                 400 gac ata aaa tac aac cgg aag att tct gcc gat ttc cac gta gac ctg      1302
Asp Ile Lys Tyr Asn Arg Lys Ile Ser Ala Asp Phe His Val Asp Leu
405                 410                 415                 420 aac cat ttc tca gtg agg caa atg ctc gcc acc acg tcc ccg gcg ctg      1350
Asn His Phe Ser Val Arg Gln Met Leu Ala Thr Thr Ser Pro Ala Leu
                425                 430                 435 atg aat ggc agt ggg cag agc cca tct gtc ctc aag ggc atc ctt cat      1398
Met Asn Gly Ser Gly Gln Ser Pro Ser Val Leu Lys Gly Ile Leu His
            440                 445                 450 gaa gcc gcc atg cag tat ccg aag cag gga ata ttt tca gtc act tgt      1446
Glu Ala Ala Met Gln Tyr Pro Lys Gln Gly Ile Phe Ser Val Thr Cys
        455                 460                 465 cct cat cca gat ata ttt ctt gtg gcc aga att gaa aaa gtc ctt cag      1494
Pro His Pro Asp Ile Phe Leu Val Ala Arg Ile Glu Lys Val Leu Gln
470                 475                 480 ggg agc atc aca cat tgc gct gag cca tat atg aaa agt tca gac tct      1542
Gly Ser Ile Thr His Cys Ala Glu Pro Tyr Met Lys Ser Ser Asp Ser
485                 490                 495                 500 tct aag gtg gcc cag aag gtg ctg aag aat gcc aag cag gca tgc caa      1590
Ser Lys Val Ala Gln Lys Val Leu Lys Asn Ala Lys Gln Ala Cys Gln
                505                 510                 515 aga cta gga cag tat aga atg cca ttt gct tgg gca gca agg aca ttg      1638
Arg Leu Gly Gln Tyr Arg Met Pro Phe Ala Trp Ala Ala Arg Thr Leu
            520                 525                 530 ttt aag gat gca tct gga aat ctt gac aaa aat gcc aga ttt tct gcc      1686
Phe Lys Asp Ala Ser Gly Asn Leu Asp Lys Asn Ala Arg Phe Ser Ala
        535                 540                 545 atc tac agg caa gac agc aat aag cta tcc aat gat gac atg ctc aag      1734
Ile Tyr Arg Gln Asp Ser Asn Lys Leu Ser Asn Asp Asp Met Leu Lys
550                 555                 560 tta ctt gca gac ttt cgg aaa cct gag aag atg gct aag ctc cca gtg      1782
Leu Leu Ala Asp Phe Arg Lys Pro Glu Lys Met Ala Lys Leu Pro Val
565                 570                 575                 580 att tta ggc aat cta gac att aca att gat aat gtt tcc tca gac ttc      1830
Ile Leu Gly Asn Leu Asp Ile Thr Ile Asp Asn Val Ser Ser Asp Phe
                585                 590                 595 cct aat tat gtt aat tca tca tac att ccc aca aaa caa ttt gaa acc      1878
Pro Asn Tyr Val Asn Ser Ser Tyr Ile Pro Thr Lys Gln Phe Glu Thr
            600                 605                 610
```

-continued

```
tgc agt aaa act ccc atc acg ttt gaa gtg gag gaa ttt gtg ccc tgc    1926
Cys Ser Lys Thr Pro Ile Thr Phe Glu Val Glu Glu Phe Val Pro Cys
        615                 620                 625 ata cca aaa cac act cag cct tac acc atc tac acc aat cac ctt tac    1974
Ile Pro Lys His Thr Gln Pro Tyr Thr Ile Tyr Thr Asn His Leu Tyr
630                 635                 640 gtt tat cct aag tac ttg aaa tac gac agt cag aag tct ttt gcc aag    2022
Val Tyr Pro Lys Tyr Leu Lys Tyr Asp Ser Gln Lys Ser Phe Ala Lys
645                 650                 655                 660 gct aga aat att gcg att tgc att gaa ttc aaa gat tca gat gag gaa    2070
Ala Arg Asn Ile Ala Ile Cys Ile Glu Phe Lys Asp Ser Asp Glu Glu
                665                 670                 675 gac tct cag ccc ctt aag tgc att tat ggc aga cct ggt ggg cca gtt    2118
Asp Ser Gln Pro Leu Lys Cys Ile Tyr Gly Arg Pro Gly Gly Pro Val
            680                 685                 690 ttc aca aga agc gcc ttt gct gca gtt tta cac cat cac caa aac cca    2166
Phe Thr Arg Ser Ala Phe Ala Ala Val Leu His His His Gln Asn Pro
        695                 700                 705 gaa ttt tat gat gag att aaa ata gag ttg ccc act cag ctg cat gaa    2214
Glu Phe Tyr Asp Glu Ile Lys Ile Glu Leu Pro Thr Gln Leu His Glu
710                 715                 720 aag cac cac ctg ttg ctc aca ttc ttc cat gtc agc tgt gac aac tca    2262
Lys His His Leu Leu Leu Thr Phe Phe His Val Ser Cys Asp Asn Ser
725                 730                 735                 740 agt aaa gga agc acg aag aag agg gat gtc gtt gaa acc caa gtt ggc    2310
Ser Lys Gly Ser Thr Lys Lys Arg Asp Val Val Glu Thr Gln Val Gly
                745                 750                 755 tac tcc tgg ctt ccc ctc ctg aaa gac gga agg gtg gtg aca agc gag    2358
Tyr Ser Trp Leu Pro Leu Leu Lys Asp Gly Arg Val Val Thr Ser Glu
            760                 765                 770 cag cac atc ccg gtc tcg gcg aac ctt cct tcg ggc tat ctt ggc tac    2406
Gln His Ile Pro Val Ser Ala Asn Leu Pro Ser Gly Tyr Leu Gly Tyr
        775                 780                 785 cag gag ctt ggg atg ggc agg cat tat ggt ccg gaa att aaa tgg gta    2454
Gln Glu Leu Gly Met Gly Arg His Tyr Gly Pro Glu Ile Lys Trp Val
    790                 795                 800 gat gga ggc aag cca ctg ctg aaa att tcc act cat ctg gtt tct aca    2502
Asp Gly Gly Lys Pro Leu Leu Lys Ile Ser Thr His Leu Val Ser Thr
805                 810                 815                 820 gtg tat act cag gat cag cat tta cat aat ttt ttc cag tac tgt cag    2550
Val Tyr Thr Gln Asp Gln His Leu His Asn Phe Phe Gln Tyr Cys Gln
                825                 830                 835 aaa acc gaa tct gga gcc caa gcc tta gga aac gaa ctt gta aag tac    2598
Lys Thr Glu Ser Gly Ala Gln Ala Leu Gly Asn Glu Leu Val Lys Tyr
            840                 845                 850 ctt aag agt ctg cat gcg atg gaa ggc cac gtg atg atc gcc ttc ttg    2646
Leu Lys Ser Leu His Ala Met Glu Gly His Val Met Ile Ala Phe Leu
        855                 860                 865 ccc act atc cta aac cag ctg ttc cga gtc ctc acc aga gcc aca cag    2694
Pro Thr Ile Leu Asn Gln Leu Phe Arg Val Leu Thr Arg Ala Thr Gln
    870                 875                 880 gaa gaa gtc gcg gtt aac gtg act cgg gtc att att cat gtg gtt gcc    2742
Glu Glu Val Ala Val Asn Val Thr Arg Val Ile Ile His Val Val Ala
885                 890                 895                 900 cag tgc cat gag gaa gga ttg gag agc cac ttg agg tca tat gtt aag    2790
Gln Cys His Glu Glu Gly Leu Glu Ser His Leu Arg Ser Tyr Val Lys
                905                 910                 915 tac gcg tat aag gct gag cca tat gtt gcc tct gaa tac aag aca gtg    2838
Tyr Ala Tyr Lys Ala Glu Pro Tyr Val Ala Ser Glu Tyr Lys Thr Val
            920                 925                 930
```

```
cat gaa gaa ctg acc aaa tcc atg acc acg att ctc aag cct tct gcc    2886
His Glu Glu Leu Thr Lys Ser Met Thr Thr Ile Leu Lys Pro Ser Ala
        935                 940                 945 gat ttc ctc acc agc aac aaa cta ctg aag tac tca tgg ttt ttc ttt    2934
Asp Phe Leu Thr Ser Asn Lys Leu Leu Lys Tyr Ser Trp Phe Phe Phe
950                 955                 960 gat gta ctg atc aaa tct atg gct cag cat ttg ata gag aac tcc aaa    2982
Asp Val Leu Ile Lys Ser Met Ala Gln His Leu Ile Glu Asn Ser Lys
965                 970                 975                 980 gtt aag ttg ctg cga aac cag aga ttt cct gca tcc tat cat cat gca    3030
Val Lys Leu Leu Arg Asn Gln Arg Phe Pro Ala Ser Tyr His His Ala
            985                 990                 995 gtg gaa acc gtt gta aat atg ctg atg cca cac atc act cag aag ttt    3078
Val Glu Thr Val Val Asn Met Leu Met Pro His Ile Thr Gln Lys Phe
        1000                1005                1010 cga gat aat cca gag gca tct aag aac gcg aat cat agc ctt gct gtc    3126
Arg Asp Asn Pro Glu Ala Ser Lys Asn Ala Asn His Ser Leu Ala Val
    1015                1020                1025 ttc atc aag aga tgt ttc acc ttc atg gac agg ggc ttt gtc ttc aag    3174
Phe Ile Lys Arg Cys Phe Thr Phe Met Asp Arg Gly Phe Val Phe Lys
1030                1035                1040 cag atc aac aac tac att agc tgt ttt gct cct gga gac cca aag acc    3222
Gln Ile Asn Asn Tyr Ile Ser Cys Phe Ala Pro Gly Asp Pro Lys Thr
1045                1050                1055                1060 ctc ttt gaa tac aag ttt gaa ttt ctc cgt gta gtg tgc aac cat gaa    3270
Leu Phe Glu Tyr Lys Phe Glu Phe Leu Arg Val Val Cys Asn His Glu
            1065                1070                1075 cat tat att ccg ttg aac tta cca atg cca ttt gga aaa ggc agg att    3318
His Tyr Ile Pro Leu Asn Leu Pro Met Pro Phe Gly Lys Gly Arg Ile
        1080                1085                1090 caa aga tac caa gac ctc cag ctt gac tac tca tta aca gat gag ttc    3366
Gln Arg Tyr Gln Asp Leu Gln Leu Asp Tyr Ser Leu Thr Asp Glu Phe
    1095                1100                1105 tgc aga aac cac ttc ttg gtg gga ctg tta ctg agg gag gtg ggg aca    3414
Cys Arg Asn His Phe Leu Val Gly Leu Leu Leu Arg Glu Val Gly Thr
1110                1115                1120 gcc ctc cag gag ttc cgg gag gtc cgt ctg atc gcc atc agt gtg ctc    3462
Ala Leu Gln Glu Phe Arg Glu Val Arg Leu Ile Ala Ile Ser Val Leu
1125                1130                1135                1140 aag aac ctg ctg ata aag cat tct ttt gat gac aga tat gct tca agg    3510
Lys Asn Leu Leu Ile Lys His Ser Phe Asp Asp Arg Tyr Ala Ser Arg
            1145                1150                1155 agc cat cag gca agg ata gcc acc ctc tac ctg cct ctg ttt ggt ctg    3558
Ser His Gln Ala Arg Ile Ala Thr Leu Tyr Leu Pro Leu Phe Gly Leu
        1160                1165                1170 ctg att gaa aac gtc cag cgg atc aat gtg agg gat gtg tca ccc ttc    3606
Leu Ile Glu Asn Val Gln Arg Ile Asn Val Arg Asp Val Ser Pro Phe
    1175                1180                1185 cct gtg aac gcg ggc atg act gtg aag gat gaa tcc ctg gct cta cca    3654
Pro Val Asn Ala Gly Met Thr Val Lys Asp Glu Ser Leu Ala Leu Pro
1190                1195                1200 gct gtg aat ccg ctg gtg acg ccg cag aag gga agc acc ctg gac aac    3702
Ala Val Asn Pro Leu Val Thr Pro Gln Lys Gly Ser Thr Leu Asp Asn
1205                1210                1215                1220 agc ctg cac aag gac ctg ctg ggc gcc atc tcc ggc att gct tct cca    3750
Ser Leu His Lys Asp Leu Leu Gly Ala Ile Ser Gly Ile Ala Ser Pro
            1225                1230                1235 tat aca acc tca act cca aac atc aac agt gtg aga aat gct gat tcg    3798
Tyr Thr Thr Ser Thr Pro Asn Ile Asn Ser Val Arg Asn Ala Asp Ser
        1240                1245                1250
```

-continued

| | | |
|---|---|---|
| aga gga tct ctc ata agc aca gat tcg ggt aac agc ctt cca gaa agg<br>Arg Gly Ser Leu Ile Ser Thr Asp Ser Gly Asn Ser Leu Pro Glu Arg<br>      1255                        1260                      1265 | 3846 | |
| aat agt gag aag agc aat tcc ctg gat aag cac caa caa agt agc aca<br>Asn Ser Glu Lys Ser Asn Ser Leu Asp Lys His Gln Gln Ser Ser Thr<br>1270                      1275                      1280 | 3894 | |
| ttg gga aat tcc gtg gtt cgc tgt gat aaa ctt gac cag tct gag att<br>Leu Gly Asn Ser Val Val Arg Cys Asp Lys Leu Asp Gln Ser Glu Ile<br>1285                      1290                      1295                    1300 | 3942 | |
| aag agc cta ctg atg tgt ttc ctc tac atc tta aag agc atg tct gat<br>Lys Ser Leu Leu Met Cys Phe Leu Tyr Ile Leu Lys Ser Met Ser Asp<br>                1305                      1310                      1315 | 3990 | |
| gat gct ttg ttt aca tat tgg aac aag gct tca aca tct gaa ctt atg<br>Asp Ala Leu Phe Thr Tyr Trp Asn Lys Ala Ser Thr Ser Glu Leu Met<br>                    1320                      1325                      1330 | 4038 | |
| gat ttt ttt aca ata tct gaa gtc tgc ctg cac cag ttc cag tac atg<br>Asp Phe Phe Thr Ile Ser Glu Val Cys Leu His Gln Phe Gln Tyr Met<br>                1335                      1340                      1345 | 4086 | |
| ggg aag cga tac ata gcc aga aca gga atg atg cat gcc aga ttg cag<br>Gly Lys Arg Tyr Ile Ala Arg Thr Gly Met Met His Ala Arg Leu Gln<br>1350                      1355                      1360 | 4134 | |
| cag ctg ggc agc ctg gat aac tct ctc act ttt aac cac agc tat ggc<br>Gln Leu Gly Ser Leu Asp Asn Ser Leu Thr Phe Asn His Ser Tyr Gly<br>1365                      1370                      1375                      1380 | 4182 | |
| cac tcg gac gca gat gtt ctg cac cag tca tta ctt gaa gcc aac att<br>His Ser Asp Ala Asp Val Leu His Gln Ser Leu Leu Glu Ala Asn Ile<br>                    1385                      1390                      1395 | 4230 | |
| gct act gag gtt tgc ctg aca gct ctg gac acg ctt tct cta ttt aca<br>Ala Thr Glu Val Cys Leu Thr Ala Leu Asp Thr Leu Ser Leu Phe Thr<br>                1400                      1405                      1410 | 4278 | |
| ttg gcg ttt aag aac cag ctc ctg gcc gac cat gga cat aat cct ctc<br>Leu Ala Phe Lys Asn Gln Leu Leu Ala Asp His Gly His Asn Pro Leu<br>1415                      1420                      1425 | 4326 | |
| atg aaa aaa gtt ttt gat gtc tac ctg tgt ttt ctt caa aaa cat cag<br>Met Lys Lys Val Phe Asp Val Tyr Leu Cys Phe Leu Gln Lys His Gln<br>1430                      1435                      1440 | 4374 | |
| tct gaa acg gct tta aaa aat gtc ttc act gcc tta agg tcc tta att<br>Ser Glu Thr Ala Leu Lys Asn Val Phe Thr Ala Leu Arg Ser Leu Ile<br>1445                      1450                      1455                      1460 | 4422 | |
| tat aag ttt ccc tca aca ttc tat gaa ggg aga gcg gac atg tgt gcg<br>Tyr Lys Phe Pro Ser Thr Phe Tyr Glu Gly Arg Ala Asp Met Cys Ala<br>                    1465                      1470                      1475 | 4470 | |
| gct ctg tgt tac gag att ctc aag tgc tgt aac tcc aag ctg agc tcc<br>Ala Leu Cys Tyr Glu Ile Leu Lys Cys Cys Asn Ser Lys Leu Ser Ser<br>                1480                      1485                      1490 | 4518 | |
| atc agg acg gag gcc tcc cag ctg ctc tac ttc ctg atg agg aac aac<br>Ile Arg Thr Glu Ala Ser Gln Leu Leu Tyr Phe Leu Met Arg Asn Asn<br>                1495                      1500                      1505 | 4566 | |
| ttt gat tac act gga aag aag tcc ttt gtc cgg aca cat ttg caa gtc<br>Phe Asp Tyr Thr Gly Lys Lys Ser Phe Val Arg Thr His Leu Gln Val<br>1510                      1515                      1520 | 4614 | |
| atc ata tct gtc agc cag ctg ata gca gac gtt gtt ggc att ggg gga<br>Ile Ile Ser Val Ser Gln Leu Ile Ala Asp Val Val Gly Ile Gly Gly<br>1525                      1530                      1535                      1540 | 4662 | |
| acc aga ttc cag cag tcc ctg tcc atc atc aac aac tgt gcc aac agt<br>Thr Arg Phe Gln Gln Ser Leu Ser Ile Ile Asn Asn Cys Ala Asn Ser<br>                    1545                      1550                      1555 | 4710 | |
| gac cgg ctt att aag cac acc agc ttc tcc tct gat gtg aag gac tta<br>Asp Arg Leu Ile Lys His Thr Ser Phe Ser Ser Asp Val Lys Asp Leu<br>                1560                      1565                      1570 | 4758 | |

```
acc aaa agg ata cgc acg gtg cta atg gcc acc gcc cag atg aag gag      4806
Thr Lys Arg Ile Arg Thr Val Leu Met Ala Thr Ala Gln Met Lys Glu
        1575                1580                1585 cat gag aac gac cca gag atg ctg gtg gac ctc cag tac agc ctg gcc      4854
His Glu Asn Asp Pro Glu Met Leu Val Asp Leu Gln Tyr Ser Leu Ala
    1590                1595                1600 aaa tcc tat gcc agc acg ccc gag ctc agg aag acg tgg ctc gac agc      4902
Lys Ser Tyr Ala Ser Thr Pro Glu Leu Arg Lys Thr Trp Leu Asp Ser
1605                1610                1615                1620 atg gcc agg atc cat gtc aaa aat ggc gat ctc tca gag gca gca atg      4950
Met Ala Arg Ile His Val Lys Asn Gly Asp Leu Ser Glu Ala Ala Met
                1625                1630                1635 tgc tat gtc cac gta aca gcc cta gtg gca gaa tat ctc aca cgg aaa      4998
Cys Tyr Val His Val Thr Ala Leu Val Ala Glu Tyr Leu Thr Arg Lys
            1640                1645                1650 gaa gca gtc cag tgg gag ccg ccc ctt ctc ccc cac agc cat agc gcc      5046
Glu Ala Val Gln Trp Glu Pro Pro Leu Leu Pro His Ser His Ser Ala
        1655                1660                1665 tgc ctg agg agg agc cgg gga ggc gtg ttt aga caa gga tgc acc gcc      5094
Cys Leu Arg Arg Ser Arg Gly Gly Val Phe Arg Gln Gly Cys Thr Ala
    1670                1675                1680 ttc agg gtc att acc cca aac atc gac gag gag gcc tcc atg atg gaa      5142
Phe Arg Val Ile Thr Pro Asn Ile Asp Glu Glu Ala Ser Met Met Glu
1685                1690                1695                1700 gac gtg ggg atg cag gat gtc cat ttc aac gag gat gtg ctg atg gag      5190
Asp Val Gly Met Gln Asp Val His Phe Asn Glu Asp Val Leu Met Glu
                1705                1710                1715 ctc ctt gag cag tgc gca gat gga ctc tgg aaa gcc gag cgc tac gag      5238
Leu Leu Glu Gln Cys Ala Asp Gly Leu Trp Lys Ala Glu Arg Tyr Glu
            1720                1725                1730 ctc att gcc gac atc tac aaa ctt atc atc ccc att tat gag aag cgg      5286
Leu Ile Ala Asp Ile Tyr Lys Leu Ile Ile Pro Ile Tyr Glu Lys Arg
        1735                1740                1745 agg gat ttt gag agg ctg gcc cat ctg tat gac acg ctg cac cgg gcc      5334
Arg Asp Phe Glu Arg Leu Ala His Leu Tyr Asp Thr Leu His Arg Ala
    1750                1755                1760 tac agc aaa gtg acc gag gtc atg cac tcg ggc cgc agg ctt ctg ggg      5382
Tyr Ser Lys Val Thr Glu Val Met His Ser Gly Arg Arg Leu Leu Gly
1765                1770                1775                1780 acc tac ttc cgg gta gcc ttc ttc ggg cag gca gcg caa tac cag ttt      5430
Thr Tyr Phe Arg Val Ala Phe Phe Gly Gln Ala Ala Gln Tyr Gln Phe
                1785                1790                1795 aca gac agt gaa aca gat gtg gag gga ttc ttt gaa gat gaa gat gga      5478
Thr Asp Ser Glu Thr Asp Val Glu Gly Phe Phe Glu Asp Glu Asp Gly
            1800                1805                1810 aag gag tat att tac aag gaa ccc aaa ctc aca ccg ctg tcg gaa att      5526
Lys Glu Tyr Ile Tyr Lys Glu Pro Lys Leu Thr Pro Leu Ser Glu Ile
        1815                1820                1825 tct cag aga ctc ctt aaa ctg tac tcg gat aaa ttt ggt tct gaa aat      5574
Ser Gln Arg Leu Leu Lys Leu Tyr Ser Asp Lys Phe Gly Ser Glu Asn
    1830                1835                1840 gtc aaa atg ata cag gat tct ggc aag gtc aac cct aag gat ctg gat      5622
Val Lys Met Ile Gln Asp Ser Gly Lys Val Asn Pro Lys Asp Leu Asp
1845                1850                1855                1860 tct aag tat gcc tac atc cag gtg act cac gtc atc ccc ttc ttt gac      5670
Ser Lys Tyr Ala Tyr Ile Gln Val Thr His Val Ile Pro Phe Phe Asp
                1865                1870                1875 gaa aaa gag ttg caa gaa agg aaa aca gag ttt gag aga tcc cac aac      5718
Glu Lys Glu Leu Gln Glu Arg Lys Thr Glu Phe Glu Arg Ser His Asn
            1880                1885                1890
```

-continued

| | |
|---|---|
| atc cgc cgc ttc atg ttt gag atg cca ttt acg cag acc ggg aag agg<br>Ile Arg Arg Phe Met Phe Glu Met Pro Phe Thr Gln Thr Gly Lys Arg<br>           1895                     1900                    1905 | 5766 |
| cag ggc ggg gtg gaa gag cag tgc aaa cgg cgc acc atc ctg aca gcc<br>Gln Gly Gly Val Glu Glu Gln Cys Lys Arg Arg Thr Ile Leu Thr Ala<br> 1910                      1915                     1920 | 5814 |
| ata cac tgc ttc cct tat gtg aag aag cgc atc cct gtc atg tac cag<br>Ile His Cys Phe Pro Tyr Val Lys Lys Arg Ile Pro Val Met Tyr Gln<br>1925                     1930                     1935                  1940 | 5862 |
| cac cac act gac ctg aac ccc atc gag gtg gcc att gac gag atg agt<br>His His Thr Asp Leu Asn Pro Ile Glu Val Ala Ile Asp Glu Met Ser<br>            1945                     1950                    1955 | 5910 |
| aag aag gtg gcg gag ctc cgg cag ctg tgc tcc tcg gcc gag gtg gac<br>Lys Lys Val Ala Glu Leu Arg Gln Leu Cys Ser Ser Ala Glu Val Asp<br> 1960                      1965                     1970 | 5958 |
| atg atc aaa ctg cag ctc aaa ctc cag ggc agc gtg agt gtt cag gtc<br>Met Ile Lys Leu Gln Leu Lys Leu Gln Gly Ser Val Ser Val Gln Val<br>          1975                     1980                    1985 | 6006 |
| aat gct ggc cca cta gca tat gcg cga gct ttc tta gat gat aca aac<br>Asn Ala Gly Pro Leu Ala Tyr Ala Arg Ala Phe Leu Asp Asp Thr Asn<br> 1990                      1995                     2000 | 6054 |
| aca aag cga tat cct gac aat aaa gtg aag ctg ctt aag gaa gtt ttc<br>Thr Lys Arg Tyr Pro Asp Asn Lys Val Lys Leu Leu Lys Glu Val Phe<br>2005                     2010                     2015                  2020 | 6102 |
| agg caa ttt gtg gaa gct tgc ggt caa gcc tta gcg gta aac gaa cgt<br>Arg Gln Phe Val Glu Ala Cys Gly Gln Ala Leu Ala Val Asn Glu Arg<br>                     2025                     2030                     2035 | 6150 |
| ctg att aaa gaa gac cag ctc gag tat cag gaa gaa atg aaa gcc aac<br>Leu Ile Lys Glu Asp Gln Leu Glu Tyr Gln Glu Glu Met Lys Ala Asn<br>            2040                     2045                    2050 | 6198 |
| tac agg gaa atg gcg aag gag ctt tct gaa atc atg cat gag cag atc<br>Tyr Arg Glu Met Ala Lys Glu Leu Ser Glu Ile Met His Glu Gln Ile<br>                     2055                     2060                     2065 | 6246 |
| tgc ccc ctg gag gag aag acg agc gtc tta ccg aat tcc ctt cac atc<br>Cys Pro Leu Glu Glu Lys Thr Ser Val Leu Pro Asn Ser Leu His Ile<br>2070                     2075                     2080 | 6294 |
| ttc aac gcc atc agt ggg act cca aca agc aca atg gtt cac ggg atg<br>Phe Asn Ala Ile Ser Gly Thr Pro Thr Ser Thr Met Val His Gly Met<br>2085                     2090                     2095                  2100 | 6342 |
| acc agc tcg tct tcg gtc gtg tga ttacatctca tggcccgtgt gtggggactt<br>Thr Ser Ser Ser Ser Val Val<br>            2105 | 6396 |
| gctttgtcat ttgcaaactc aggatgcttt ccaaagccaa tcactgggga gaccgagcac | 6456 |
| agggaggacc aggggaaggg gagagaaagg aaataaagaa caacgttatt tcttaacaga | 6516 |
| cttttctatag gagttgtaag aaggtgcaca tatttttta aatctcactg gcaatattca | 6576 |
| aagttttcat tgtgtcttaa caaaggtgtg gtagacactc ttgagctgga cttagatttt | 6636 |
| attcttcctt gcagagtagt gttagaatag atggcctaca gaaaaaaaag gttctgggat | 6696 |
| ctacatggca gggagggctg cactgacatt gatgcctggg ggacctttg cctcgaggct | 6756 |
| gagctggaaa atcttgaaaa tattttttt ttcctgtggc acattcaggt tgaatacaag | 6816 |
| aactatttt gtgactagtt tttgatgacc taagggaact gaccattgta attttgtac | 6876 |
| cagtgaacca ggagatttag tgcttttata ttcatttcct tgcatttaag aaaatatgaa | 6936 |
| agcttaagga attatgtgag cttaaaacta gtcaagcagt ttagaaccaa aggcctatat | 6996 |
| taataaccgc aactatgctg aaaagtacaa agtagtacag tatattgtta tgtacatatc | 7056 |
| attgttaata cagtcctggc attctgtaca tatatgtatt acatttctac atttttaata | 7116 |

```
ctcacatggg cttatgcatt aagtttaatt gtgataaatt tgtgctgttc cagtatatgc    7176
aatacacttt aatgttttat tcttgtacat aaaaatgtgc aatatggaga gtatacagt     7236 ctttactata ttaggtttat aaacagtttt aagaatttca tccttttgcc aaaatggtgg    7296
agtatgtaat tggtaaatca taaatcctgt ggtgaatggt ggtgtacttt aaagctgtca    7356
ccatgttata ttttctttta agacattaat ttagtaattt tatatttggg aaaataaagg    7416
tttttaattt tatttaactg gaatcactgc cctgctgtaa ttaaacattc tgtaccacat    7476
ctgtattaaa aagacattgc tgac                                           7500
```

<210> SEQ ID NO 2
<211> LENGTH: 2107
<212> TYPE: PRT
<213> ORGANISM: Homo sapiens

<400> SEQUENCE: 2

```
Met Ser Gln Pro Pro Leu Leu Pro Ala Ser Ala Glu Thr Arg Lys Phe
  1               5                  10                  15

Thr Arg Ala Leu Ser Lys Pro Gly Thr Ala Ala Glu Leu Arg Gln Ser
             20                  25                  30

Val Ser Glu Val Val Arg Gly Ser Val Leu Leu Ala Lys Pro Lys Leu
         35                  40                  45

Ile Glu Pro Leu Asp Tyr Glu Asn Val Ile Val Gln Lys Lys Thr Gln
     50                  55                  60

Ile Leu Asn Asp Cys Leu Arg Glu Met Leu Leu Phe Pro Tyr Asp Asp
 65                  70                  75                  80

Phe Gln Thr Ala Ile Leu Arg Arg Gln Gly Arg Tyr Ile Cys Ser Thr
                 85                  90                  95

Val Pro Ala Lys Ala Glu Glu Ala Gln Ser Leu Phe Val Thr Glu
            100                 105                 110

Cys Ile Lys Thr Tyr Asn Ser Asp Trp His Leu Val Asn Tyr Lys Tyr
            115                 120                 125

Glu Asp Tyr Ser Gly Glu Phe Arg Gln Leu Pro Asn Lys Val Val Lys
        130                 135                 140

Leu Asp Lys Leu Pro Val His Val Tyr Glu Val Asp Glu Glu Val Asp
145                 150                 155                 160

Lys Asp Glu Asp Ala Ala Ser Leu Gly Ser Gln Lys Gly Gly Ile Thr
                165                 170                 175

Lys His Gly Trp Leu Tyr Lys Gly Asn Met Asn Ser Ala Ile Ser Val
            180                 185                 190

Thr Met Arg Ser Phe Lys Arg Arg Phe Phe His Leu Ile Gln Leu Gly
        195                 200                 205

Asp Gly Ser Tyr Asn Leu Asn Phe Tyr Lys Asp Glu Lys Ile Ser Lys
    210                 215                 220

Glu Pro Lys Gly Ser Ile Phe Leu Asp Ser Cys Met Gly Val Val Gln
225                 230                 235                 240

Asn Asn Lys Val Arg Arg Phe Ala Phe Glu Leu Lys Met Gln Asp Lys
                245                 250                 255

Ser Ser Tyr Leu Leu Ala Ala Asp Ser Glu Val Glu Met Glu Glu Trp
            260                 265                 270

Ile Thr Ile Leu Asn Lys Ile Leu Gln Leu Asn Phe Glu Ala Ala Met
        275                 280                 285

Gln Glu Lys Arg Asn Gly Asp Ser His Glu Asp Asp Glu Gln Ser Lys
    290                 295                 300
```

-continued

```
Leu Glu Gly Ser Gly Ser Gly Leu Asp Ser Tyr Leu Pro Glu Leu Ala
305                 310                 315                 320

Lys Ser Ala Arg Glu Ala Glu Ile Lys Leu Lys Ser Glu Ser Arg Val
            325                 330                 335

Lys Leu Phe Tyr Leu Asp Pro Asp Ala Gln Lys Leu Asp Phe Ser Ser
        340                 345                 350

Ala Glu Pro Glu Val Lys Ser Phe Glu Lys Phe Gly Lys Arg Ile
    355                 360                 365

Leu Val Lys Cys Asn Asp Leu Ser Phe Asn Leu Gln Cys Cys Val Ala
    370                 375                 380

Glu Asn Glu Glu Gly Pro Thr Thr Asn Val Glu Pro Phe Phe Val Thr
385                 390                 395                 400

Leu Ser Leu Phe Asp Ile Lys Tyr Asn Arg Lys Ile Ser Ala Asp Phe
                405                 410                 415

His Val Asp Leu Asn His Phe Ser Val Arg Gln Met Leu Ala Thr Thr
            420                 425                 430

Ser Pro Ala Leu Met Asn Gly Ser Gly Gln Ser Pro Ser Val Leu Lys
        435                 440                 445

Gly Ile Leu His Glu Ala Ala Met Gln Tyr Pro Lys Gln Gly Ile Phe
    450                 455                 460

Ser Val Thr Cys Pro His Pro Asp Ile Phe Leu Val Ala Arg Ile Glu
465                 470                 475                 480

Lys Val Leu Gln Gly Ser Ile Thr His Cys Ala Glu Pro Tyr Met Lys
                485                 490                 495

Ser Ser Asp Ser Ser Lys Val Ala Gln Lys Val Leu Lys Asn Ala Lys
            500                 505                 510

Gln Ala Cys Gln Arg Leu Gly Gln Tyr Arg Met Pro Phe Ala Trp Ala
        515                 520                 525

Ala Arg Thr Leu Phe Lys Asp Ala Ser Gly Asn Leu Asp Lys Asn Ala
    530                 535                 540

Arg Phe Ser Ala Ile Tyr Arg Gln Asp Ser Asn Lys Leu Ser Asn Asp
545                 550                 555                 560

Asp Met Leu Lys Leu Leu Ala Asp Phe Arg Lys Pro Glu Lys Met Ala
                565                 570                 575

Lys Leu Pro Val Ile Leu Gly Asn Leu Asp Ile Thr Ile Asp Asn Val
            580                 585                 590

Ser Ser Asp Phe Pro Asn Tyr Val Asn Ser Ser Tyr Ile Pro Thr Lys
        595                 600                 605

Gln Phe Glu Thr Cys Ser Lys Thr Pro Ile Thr Phe Glu Val Glu Glu
    610                 615                 620

Phe Val Pro Cys Ile Pro Lys His Thr Gln Pro Tyr Thr Ile Tyr Thr
625                 630                 635                 640

Asn His Leu Tyr Val Tyr Pro Lys Tyr Leu Lys Tyr Asp Ser Gln Lys
                645                 650                 655

Ser Phe Ala Lys Ala Arg Asn Ile Ala Ile Cys Ile Glu Phe Lys Asp
            660                 665                 670

Ser Asp Glu Glu Asp Ser Gln Pro Leu Lys Cys Ile Tyr Gly Arg Pro
        675                 680                 685

Gly Gly Pro Val Phe Thr Arg Ser Ala Phe Ala Ala Val Leu His His
    690                 695                 700

His Gln Asn Pro Glu Phe Tyr Asp Glu Ile Lys Ile Glu Leu Pro Thr
705                 710                 715                 720
```

-continued

```
Gln Leu His Glu Lys His His Leu Leu Leu Thr Phe Phe His Val Ser
            725                 730                 735
Cys Asp Asn Ser Ser Lys Gly Ser Thr Lys Lys Arg Asp Val Val Glu
            740                 745                 750
Thr Gln Val Gly Tyr Ser Trp Leu Pro Leu Leu Lys Asp Gly Arg Val
            755                 760                 765
Val Thr Ser Glu Gln His Ile Pro Val Ser Ala Asn Leu Pro Ser Gly
770                 775                 780
Tyr Leu Gly Tyr Gln Glu Leu Gly Met Gly Arg His Tyr Gly Pro Glu
785                 790                 795                 800
Ile Lys Trp Val Asp Gly Lys Pro Leu Leu Lys Ile Ser Thr His
            805                 810                 815
Leu Val Ser Thr Val Tyr Thr Gln Asp Gln His Leu His Asn Phe Phe
            820                 825                 830
Gln Tyr Cys Gln Lys Thr Glu Ser Gly Ala Gln Ala Leu Gly Asn Glu
            835                 840                 845
Leu Val Lys Tyr Leu Lys Ser Leu His Ala Met Glu Gly His Val Met
850                 855                 860
Ile Ala Phe Leu Pro Thr Ile Leu Asn Gln Leu Phe Arg Val Leu Thr
865                 870                 875                 880
Arg Ala Thr Gln Glu Glu Val Ala Val Asn Val Thr Arg Val Ile Ile
            885                 890                 895
His Val Val Ala Gln Cys His Glu Glu Gly Leu Glu Ser His Leu Arg
            900                 905                 910
Ser Tyr Val Lys Tyr Ala Tyr Lys Ala Glu Pro Tyr Val Ala Ser Glu
            915                 920                 925
Tyr Lys Thr Val His Glu Glu Leu Thr Lys Ser Met Thr Thr Ile Leu
            930                 935                 940
Lys Pro Ser Ala Asp Phe Leu Thr Ser Asn Lys Leu Leu Lys Tyr Ser
945                 950                 955                 960
Trp Phe Phe Phe Asp Val Leu Ile Lys Ser Met Ala Gln His Leu Ile
            965                 970                 975
Glu Asn Ser Lys Val Lys Leu Leu Arg Asn Gln Arg Phe Pro Ala Ser
            980                 985                 990
Tyr His His Ala Val Glu Thr Val Val Asn Met Leu Met Pro His Ile
            995                 1000                1005
Thr Gln Lys Phe Arg Asp Asn Pro Glu Ala Ser Lys Asn Ala Asn His
        1010                1015                1020
Ser Leu Ala Val Phe Ile Lys Arg Cys Phe Thr Phe Met Asp Arg Gly
1025                1030                1035                1040
Phe Val Phe Lys Gln Ile Asn Asn Tyr Ile Ser Cys Phe Ala Pro Gly
                1045                1050                1055
Asp Pro Lys Thr Leu Phe Glu Tyr Lys Phe Glu Phe Leu Arg Val Val
                1060                1065                1070
Cys Asn His Glu His Tyr Ile Pro Leu Asn Leu Pro Met Pro Phe Gly
                1075                1080                1085
Lys Gly Arg Ile Gln Arg Tyr Gln Asp Leu Gln Leu Asp Tyr Ser Leu
                1090                1095                1100
Thr Asp Glu Phe Cys Arg Asn His Phe Leu Val Gly Leu Leu Leu Arg
1105                1110                1115                1120
Glu Val Gly Thr Ala Leu Gln Glu Phe Arg Glu Val Arg Leu Ile Ala
                1125                1130                1135
```

-continued

Ile Ser Val Leu Lys Asn Leu Leu Ile Lys His Ser Phe Asp Asp Arg
            1140                1145                1150

Tyr Ala Ser Arg Ser His Gln Ala Arg Ile Ala Thr Leu Tyr Leu Pro
        1155                1160                1165

Leu Phe Gly Leu Leu Ile Glu Asn Val Gln Arg Ile Asn Val Arg Asp
    1170                1175                1180

Val Ser Pro Phe Pro Val Asn Ala Gly Met Thr Val Lys Asp Glu Ser
1185                1190                1195                1200

Leu Ala Leu Pro Ala Val Asn Pro Leu Val Thr Pro Gln Lys Gly Ser
            1205                1210                1215

Thr Leu Asp Asn Ser Leu His Lys Asp Leu Leu Gly Ala Ile Ser Gly
        1220                1225                1230

Ile Ala Ser Pro Tyr Thr Thr Ser Thr Pro Asn Ile Asn Ser Val Arg
    1235                1240                1245

Asn Ala Asp Ser Arg Gly Ser Leu Ile Ser Thr Asp Ser Gly Asn Ser
1250                1255                1260

Leu Pro Glu Arg Asn Ser Glu Lys Ser Asn Ser Leu Asp Lys His Gln
1265                1270                1275                1280

Gln Ser Ser Thr Leu Gly Asn Ser Val Val Arg Cys Asp Lys Leu Asp
        1285                1290                1295

Gln Ser Glu Ile Lys Ser Leu Leu Met Cys Phe Leu Tyr Ile Leu Lys
    1300                1305                1310

Ser Met Ser Asp Asp Ala Leu Phe Thr Tyr Trp Asn Lys Ala Ser Thr
    1315                1320                1325

Ser Glu Leu Met Asp Phe Phe Thr Ile Ser Glu Val Cys Leu His Gln
    1330                1335                1340

Phe Gln Tyr Met Gly Lys Arg Tyr Ile Ala Arg Thr Gly Met Met His
1345                1350                1355                1360

Ala Arg Leu Gln Gln Leu Gly Ser Leu Asp Asn Ser Leu Thr Phe Asn
        1365                1370                1375

His Ser Tyr Gly His Ser Asp Ala Asp Val Leu His Gln Ser Leu Leu
    1380                1385                1390

Glu Ala Asn Ile Ala Thr Glu Val Cys Leu Thr Ala Leu Asp Thr Leu
    1395                1400                1405

Ser Leu Phe Thr Leu Ala Phe Lys Asn Gln Leu Leu Ala Asp His Gly
    1410                1415                1420

His Asn Pro Leu Met Lys Lys Val Phe Asp Val Tyr Leu Cys Phe Leu
1425                1430                1435                1440

Gln Lys His Gln Ser Glu Thr Ala Leu Lys Asn Val Phe Thr Ala Leu
        1445                1450                1455

Arg Ser Leu Ile Tyr Lys Phe Pro Ser Thr Phe Tyr Glu Gly Arg Ala
        1460                1465                1470

Asp Met Cys Ala Ala Leu Cys Tyr Glu Ile Leu Lys Cys Cys Asn Ser
    1475                1480                1485

Lys Leu Ser Ser Ile Arg Thr Glu Ala Ser Gln Leu Leu Tyr Phe Leu
    1490                1495                1500

Met Arg Asn Asn Phe Asp Tyr Thr Gly Lys Lys Ser Phe Val Arg Thr
1505                1510                1515                1520

His Leu Gln Val Ile Ile Ser Val Ser Gln Leu Ile Ala Asp Val Val
            1525                1530                1535

Gly Ile Gly Gly Thr Arg Phe Gln Gln Ser Leu Ser Ile Ile Asn Asn
        1540                1545                1550

-continued

Cys Ala Asn Ser Asp Arg Leu Ile Lys His Thr Ser Phe Ser Ser Asp
    1555                1560                1565

Val Lys Asp Leu Thr Lys Arg Ile Arg Thr Val Leu Met Ala Thr Ala
1570                1575                1580

Gln Met Lys Glu His Glu Asn Asp Pro Glu Met Leu Val Asp Leu Gln
1585                1590                1595                1600

Tyr Ser Leu Ala Lys Ser Tyr Ala Ser Thr Pro Glu Leu Arg Lys Thr
            1605                1610                1615

Trp Leu Asp Ser Met Ala Arg Ile His Val Lys Asn Gly Asp Leu Ser
                1620                1625                1630

Glu Ala Ala Met Cys Tyr Val His Val Thr Ala Leu Val Ala Glu Tyr
            1635                1640                1645

Leu Thr Arg Lys Glu Ala Val Gln Trp Glu Pro Pro Leu Leu Pro His
        1650                1655                1660

Ser His Ser Ala Cys Leu Arg Arg Ser Arg Gly Gly Val Phe Arg Gln
1665                1670                1675                1680

Gly Cys Thr Ala Phe Arg Val Ile Thr Pro Asn Ile Asp Glu Glu Ala
            1685                1690                1695

Ser Met Met Glu Asp Val Gly Met Gln Asp Val His Phe Asn Glu Asp
        1700                1705                1710

Val Leu Met Glu Leu Leu Glu Gln Cys Ala Asp Gly Leu Trp Lys Ala
    1715                1720                1725

Glu Arg Tyr Glu Leu Ile Ala Asp Ile Tyr Lys Leu Ile Ile Pro Ile
    1730                1735                1740

Tyr Glu Lys Arg Arg Asp Phe Glu Arg Leu Ala His Leu Tyr Asp Thr
1745                1750                1755                1760

Leu His Arg Ala Tyr Ser Lys Val Thr Glu Val Met His Ser Gly Arg
            1765                1770                1775

Arg Leu Leu Gly Thr Tyr Phe Arg Val Ala Phe Phe Gly Gln Ala Ala
        1780                1785                1790

Gln Tyr Gln Phe Thr Asp Ser Glu Thr Asp Val Glu Gly Phe Phe Glu
    1795                1800                1805

Asp Glu Asp Gly Lys Glu Tyr Ile Tyr Lys Glu Pro Lys Leu Thr Pro
    1810                1815                1820

Leu Ser Glu Ile Ser Gln Arg Leu Leu Lys Leu Tyr Ser Asp Lys Phe
1825                1830                1835                1840

Gly Ser Glu Asn Val Lys Met Ile Gln Asp Ser Gly Lys Val Asn Pro
            1845                1850                1855

Lys Asp Leu Asp Ser Lys Tyr Ala Tyr Ile Gln Val Thr His Val Ile
        1860                1865                1870

Pro Phe Phe Asp Glu Lys Glu Leu Gln Glu Arg Lys Thr Glu Phe Glu
    1875                1880                1885

Arg Ser His Asn Ile Arg Arg Phe Met Phe Glu Met Pro Phe Thr Gln
    1890                1895                1900

Thr Gly Lys Arg Gln Gly Gly Val Glu Glu Gln Cys Lys Arg Arg Thr
1905                1910                1915                1920

Ile Leu Thr Ala Ile His Cys Phe Pro Tyr Val Lys Lys Arg Ile Pro
            1925                1930                1935

Val Met Tyr Gln His His Thr Asp Leu Asn Pro Ile Glu Val Ala Ile
        1940                1945                1950

Asp Glu Met Ser Lys Lys Val Ala Glu Leu Arg Gln Leu Cys Ser Ser
    1955                1960                1965

```
Ala Glu Val Asp Met Ile Lys Leu Gln Leu Lys Leu Gln Gly Ser Val
    1970                1975                1980

Ser Val Gln Val Asn Ala Gly Pro Leu Ala Tyr Ala Arg Ala Phe Leu
1985                1990                1995                2000

Asp Asp Thr Asn Thr Lys Arg Tyr Pro Asp Asn Lys Val Lys Leu Leu
                2005                2010                2015

Lys Glu Val Phe Arg Gln Phe Val Glu Ala Cys Gly Gln Ala Leu Ala
            2020                2025                2030

Val Asn Glu Arg Leu Ile Lys Glu Asp Gln Leu Glu Tyr Gln Glu Glu
        2035                2040                2045

Met Lys Ala Asn Tyr Arg Glu Met Ala Lys Glu Leu Ser Glu Ile Met
    2050                2055                2060

His Glu Gln Ile Cys Pro Leu Glu Glu Lys Thr Ser Val Leu Pro Asn
2065                2070                2075                2080

Ser Leu His Ile Phe Asn Ala Ile Ser Gly Thr Pro Thr Ser Thr Met
                2085                2090                2095

Val His Gly Met Thr Ser Ser Ser Ser Val Val
            2100                2105

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Primer 1

<400> SEQUENCE: 3
ttttgtcgac catggcggtg gcggacctcg                                      30

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Primer 2

<400> SEQUENCE: 4
ttttgcggcc gctcagtagc cgtcgttagc c                                    31

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Primer 3

<400> SEQUENCE: 5
aattccaggt cgacctcgag gcggccgct                                       29

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Primer 4

<400> SEQUENCE: 6
tcgaaccggc cgcctcgagg tcgacctgg                                       29
```

<210> SEQ ID NO 7
<211> LENGTH: 276
<212> TYPE: PRT
<213> ORGANISM: Artificial Sequence
<220> FEATURE:
<223> OTHER INFORMATION: Description of Artificial Sequence:
       Fusionprotein Gal4-PHP1

<400> SEQUENCE: 7

```
Met Lys Leu Leu Ser Ser Ile Glu Gln Ala Cys Asp Ile Cys Arg Leu
  1               5                  10                  15

Lys Lys Leu Lys Cys Ser Lys Glu Lys Pro Lys Cys Ala Lys Cys Leu
             20                  25                  30

Lys Asn Asn Trp Glu Cys Arg Tyr Ser Pro Lys Thr Lys Arg Ser Pro
         35                  40                  45

Leu Thr Arg Ala His Leu Thr Glu Val Glu Ser Arg Leu Glu Arg Leu
     50                  55                  60

Glu Gln Leu Phe Leu Leu Ile Phe Pro Arg Glu Asp Leu Asp Met Ile
 65                  70                  75                  80

Leu Lys Met Asp Ser Leu Gln Asp Ile Lys Ala Leu Leu Thr Gly Leu
                 85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ser Arg Ser Thr Met Ala Val Ala Asp Leu Ala Leu Ile
145                 150                 155                 160

Pro Asp Val Asp Ile Asp Ser Asp Gly Val Phe Lys Tyr Val Leu Ile
                165                 170                 175

Arg Val His Ser Ala Pro Arg Ser Gly Ala Pro Ala Ala Glu Ser Lys
            180                 185                 190

Glu Ile Val Arg Gly Tyr Lys Trp Ala Glu Tyr His Ala Asp Ile Tyr
        195                 200                 205

Asp Lys Val Ser Gly Asp Met Gln Lys Gln Gly Cys Asp Cys Glu Cys
    210                 215                 220

Leu Gly Gly Arg Ile Ser His Gln Ser Gln Asp Lys Lys Ile His
225                 230                 235                 240

Val Tyr Gly Tyr Ser Met Ala Tyr Gly Pro Ala Gln His Ala Ile Ser
                245                 250                 255

Thr Glu Lys Ile Lys Ala Lys Tyr Pro Asp Tyr Glu Val Thr Trp Ala
            260                 265                 270

Asn Asp Gly Tyr
        275
```

<210> SEQ ID NO 8
<211> LENGTH: 332
<212> TYPE: PRT
<213> ORGANISM: Artificial Sequence
<220> FEATURE:
<223> OTHER INFORMATION: Description of Artificial Sequence:
       Fusionprotein LexA-PHP1

<400> SEQUENCE: 8

```
Met Lys Ala Leu Thr Ala Arg Gln Gln Glu Val Phe Asp Leu Ile Arg
  1               5                  10                  15
```

```
Asp His Ile Ser Gln Thr Gly Met Pro Pro Thr Arg Ala Glu Ile Ala
             20                  25                  30

Gln Arg Leu Gly Phe Arg Ser Pro Asn Ala Ala Glu His Leu Lys
         35                  40                  45

Ala Leu Ala Arg Lys Gly Val Ile Glu Ile Val Ser Gly Ala Ser Arg
 50                  55                  60

Gly Ile Arg Leu Leu Gln Glu Glu Glu Gly Leu Pro Leu Val Gly
 65                  70                  75                  80

Arg Val Ala Ala Gly Glu Pro Leu Leu Ala Gln Gln His Ile Glu Gly
                 85                  90                  95

His Tyr Gln Val Asp Pro Ser Leu Phe Lys Pro Asn Ala Asp Phe Leu
             100                 105                 110

Leu Arg Val Ser Gly Met Ser Met Lys Asp Ile Gly Ile Met Asp Gly
         115                 120                 125

Asp Leu Leu Ala Val His Lys Thr Gln Asp Val Arg Asn Gly Gln Val
 130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                 165                 170                 175

Ile Val Val Asp Leu Arg Gln Gln Ser Phe Thr Ile Glu Gly Leu Ala
             180                 185                 190

Val Gly Val Ile Arg Asn Gly Asp Trp Leu Glu Phe Arg Ser Thr Met
         195                 200                 205

Ala Val Ala Asp Leu Ala Leu Ile Pro Asp Val Asp Ile Asp Ser Asp
 210                 215                 220

Gly Val Phe Lys Tyr Val Leu Ile Arg Val His Ser Ala Pro Arg Ser
225                 230                 235                 240

Gly Ala Pro Ala Ala Glu Ser Lys Glu Ile Val Arg Gly Tyr Lys Trp
                 245                 250                 255

Ala Glu Tyr His Ala Asp Ile Tyr Asp Lys Val Ser Gly Asp Met Gln
             260                 265                 270

Lys Gln Gly Cys Asp Cys Glu Cys Leu Gly Gly Arg Ile Ser His
         275                 280                 285

Gln Ser Gln Asp Lys Lys Ile His Val Tyr Gly Tyr Ser Met Ala Tyr
290                 295                 300

Gly Pro Ala Gln His Ala Ile Ser Thr Glu Lys Ile Lys Ala Lys Tyr
305                 310                 315                 320

Pro Asp Tyr Glu Val Thr Trp Ala Asn Asp Gly Tyr
                 325                 330

<210> SEQ ID NO 9
<211> LENGTH: 124
<212> TYPE: PRT
<213> ORGANISM: Homo sapiens

<400> SEQUENCE: 9

Ala Val Ala Asp Leu Ala Leu Ile Pro Asp Val Asp Ile Asp Ser Asp
 1               5                  10                  15

Gly Val Phe Lys Tyr Val Leu Ile Arg Val His Ser Ala Pro Arg Ser
             20                  25                  30

Gly Ala Pro Ala Ala Glu Ser Lys Glu Ile Val Arg Gly Tyr Lys Trp
         35                  40                  45

Ala Glu Tyr His Ala Asp Ile Tyr Asp Lys Val Ser Gly Asp Met Gln
 50                  55                  60
```

```
Lys Gln Gly Cys Asp Cys Glu Cys Leu Gly Gly Gly Arg Ile Ser His
 65              70                  75                  80

Gln Ser Gln Asp Lys Lys Ile His Val Tyr Gly Tyr Ser Met Ala Tyr
             85                  90                  95

Gly Pro Ala Gln His Ala Ile Ser Thr Glu Lys Ile Lys Ala Lys Tyr
            100             105                 110

Pro Asp Tyr Glu Val Thr Trp Ala Asn Asp Gly Tyr
        115                 120
```

HISTIDINE PHOSPHATASE INTERACTING PROTEIN WITH 240KD

FIELD OF THE INVENTION

This invention relates to newly identified polypeptides and polynucleotides encoding such polypeptides sometimes hereinafter referred to as "novel Protein Histidine Phosphatase Interacting Partner of 240 kD (PHPIP-240)", to their use in diagnosis and in identifying compounds that may be agonists, antagonists that are potentially useful in therapy, and to production of such polypeptides and polynucleotides.

BACKGROUND OF THE INVENTION

Functional genomics relies heavily on high-throughput and the various tools of bioinformatics to identify gene sequences of potential interest from the many molecular biology databases now available. There is a continuing need to identify and characterise further genes and their related polypeptides/proteins, as targets for drug discovery.

Recently, the first human protein histidine phosphatase (PHP1) has been identified. The enzyme was isolated from rabbit liver extracts and characterized. In human cell lines PHP1 is displayed in the cytoplasma. Functional studies with the orthologue protein in C.elegans showed a neuronal localization. The C.elegans homologue of PHP1 has been localized in motor- and pharyngeal sensorineurons MC, M3 and I2. The analogy from a nematode's pharynx to the human heart is described (PNAS 1998 95,5072–5) thus, PHP1 and ligand could be relevant for various cardiovascular diseases.

In the current application protein interaction studies with PHP1 have been used in combination with DNA sequencing technologies and bioinformatics to identify gene sequences and gene functions that are ligands and interaction partners of PHP-1 on a molecular level.

SUMMARY OF THE INVENTION

Protein interaction studies with PHP1 the protein kiaa 1058 (PHPIP-240) as a yet unknown interaction partners.

The present invention relates to PHPIP-240, in particular PHPIP-240 polypeptides and PHPIP-240 polynucleotides, recombinant materials and methods for their production. Such polypeptides and polynucleotides are of interest in relation to methods of treatment of certain diseases, including, but not limited to autismus: a defect in nerve cells membrane activity linked to the fatty acid metabolim (Am J Med Genet. 2000 Dec. 4;96(6):765–70), schizophrenia (Psychiatr Q 1994 Winter;65(4):287–97), familial recurrent arthritis (Arthritis Rheum 2000 September;43(9):2041–5), Bardet-Biedl Syndrome (BBS4) (Genomics 1997 Apr. 1;41(1):93–9), congenital dyserythropoietic anemia type III (Haematologica 2000 85,753–7), and Malignant fibrous histocytomas where comparative genomic hybridization (CGH) profiles identified chromosome 15q22-q26 as well as the locus of PHPIP-240 chromosome 13q32-q34 as the most frequent imbalance in this tissue sarcoma (Cancer Genet Cytogenet 1999; 111,134–8) hereinafter referred to as "diseases of the invention". In a further aspect, the invention relates to methods for identifying agonists and antagonists (e.g., inhibitors) using the materials provided by the invention, and treating conditions associated with PHPIP-240 imbalance with the identified compounds. In a still further aspect, the invention relates to diagnostic assays for detecting diseases associated with inappropriate PHPIP-240 activity or levels.

DESCRIPTION OF THE INVENTION

In a first aspect, the present invention relates to PHPIP-240 polypeptides. Such polypeptides include:
(a) an isolated polypeptide encoded by a polynucleotide comprising the sequence of SEQ ID NO:1;
(b) an isolated polypeptide comprising a polypeptide sequence having at least 95%, 96%, 97%, 98%, or 99% identity to the polypeptide sequence of SEQ ID NO:2;
(c) an isolated polypeptide comprising the polypeptide sequence of SEQ ID NO:2;
(d) an isolated polypeptide having at least 95%, 96%, 97%, 98%, or 99% identity to the polypeptide sequence of SEQ ID NO:2;
(e) the polypeptide sequence of SEQ ID NO:2; and
(f) an isolated polypeptide having or comprising a polypeptide sequence that has an Identity Index of 0.95, 0.96, 0.97, 0.98, or 0.99 compared to the polypeptide sequence of SEQ ID NO:2;
(g) fragments and variants of such polypeptides in (a) to (f).

Polypeptides of the present invention are members of the PHPIP-240 family of polypeptides. PHPIP-240 is therefore of interest because they are ligands for human protein histidine phosphatase (PHP1). Hisitidine phosphorylation in mammals is involved in signal transduction via multimeric protein complexes. In human cell lines PHP1 is displayed in the cytoplasma of cells with neuronal localization, however other cell types outside that location do express it as well. Thus the new ligand is relevant for other diseases and especially for various cardiovascular disorders.

The biological properties of the PHPIP-240 are hereinafter referred to as "biological activity of PHPIP-240" or "PHPIP-240 activity". Preferably, a polypeptide of the present invention exhibits at least one biological activity of PHPIP-240.

Polypeptides of the present invention also includes variants of the aforementioned polypeptides, including all allelic forms and splice variants. Such polypeptides vary from the reference polypeptide by insertions, deletions, and substitutions that may be conservative or non-conservative, or any combination thereof. Particularly preferred variants are those in which several, for instance from 50 to 30, from 30 to 20, from 20 to 10, from 10 to 5, from 5 to 3, from 3 to 2, from 2 to 1 or 1 amino acids are inserted, substituted, or deleted, in any combination.

Preferred fragments of polypeptides of the present invention include an isolated polypeptide comprising an amino acid sequence having at least 30, 50 or 100 contiguous amino acids from the amino acid sequence of SEQ ID NO: 2, or an isolated polypeptide comprising an amino acid sequence having at least 30, 50 or 100 contiguous amino acids truncated or deleted from the amino acid sequence of SEQ ID NO: 2. Preferred fragments are biologically active fragments that mediate the biological activity of PHPIP-240, including those with a similar activity or an improved activity, or with a decreased undesirable activity. Also preferred are those fragments that are antigenic or immunogenic in an animal, especially in a human.

Fragments of the polypeptides of the invention may be employed for producing the corresponding full-length polypeptide by peptide synthesis; therefore, these variants may be employed as intermediates for producing the full-length polypeptides of the invention. The polypeptides of the present invention may be in the form of the "mature" protein or may be a part of a larger protein such as a precursor or a fusion protein. It is often advantageous to include an additional amino acid sequence that contains secretory or leader sequences, pro-sequences, sequences that aid in purification, for instance multiple histidine residues, or an additional sequence for stability during recombinant production.

Polypeptides of the present invention can be prepared in any suitable manner, for instance by isolation form naturally occurring sources, from genetically engineered host cells comprising expression systems (vide infra) or by chemical synthesis, using for instance automated peptide synthesizers, or a combination of such methods. Means for preparing such polypeptides are well understood in the art.

In a further aspect, the present invention relates to PHPIP-240 polynucleotides. Such polynucleotides include:
(a) an isolated polynucleotide comprising a polynucleotide sequence having at least 95%, 96%, 97%, 98%, or 99% identity to the polynucleotide sequence of SEQ ID NO:1;
(b) an isolated polynucleotide comprising the polynucleotide of SEQ ID NO:1;
(c) an isolated polynucleotide having at least 95%, 96%, 97%, 98%, or 99% identity to the polynucleotide of SEQ ID NO:1;
(d) the isolated polynucleotide of SEQ ID NO:1;
(e) an isolated polynucleotide comprising a polynucleotide sequence encoding a polypeptide sequence having at least 95%, 96%, 97%, 98%, or 99% identity to the polypeptide sequence of SEQ ID NO:2;
(f) an isolated polynucleotide comprising a polynucleotide sequence encoding the polypeptide of SEQ ID NO:2;
(g) an isolated polynucleotide having a polynucleotide sequence encoding a polypeptide sequence having at least 95%, 96%, 97%, 98%, or 99% identity to the polypeptide sequence of SEQ ID NO:2;
(h) an isolated polynucleotide encoding the polypeptide of SEQ ID NO:2;
(i) an isolated polynucleotide having or comprising a polynucleotide sequence that has an Identity Index of 0.95, 0.96, 0.97, 0.98, or 0.99 compared to the polynucleotide sequence of SEQ ID NO:1;
(j) an isolated polynucleotide having or comprising a polynucleotide sequence encoding a polypeptide sequence that has an Identity Index of 0.95, 0.96, 0.97, 0.98, or 0.99 compared to the polypeptide sequence of SEQ ID NO:2; and
polynucleotides that are fragments and variants of the above mentioned polynucleotides or that are complementary to above mentioned polynucleotides, over the entire length thereof.

Preferred fragments of polynucleotides of the present invention include an isolated polynucleotide comprising an nucleotide sequence having at least 15, 30, 50 or 100 contiguous nucleotides from the sequence of SEQ ID NO: 1, or an isolated polynucleotide comprising an sequence having at least 30, 50 or 100 contiguous nucleotides truncated or deleted from the sequence of SEQ ID NO: 1.

Preferred variants of polynucleotides of the present invention include splice variants, allelic variants, and polymorphisms, including polynucleotides having one or more single nucleotide polymorphisms (SNPs).

Polynucleotides of the present invention also include polynucleotides encoding polypeptide variants that comprise the amino acid sequence of SEQ ID NO:2 and in which several, for instance from 50 to 30, from 30 to 20, from 20 to 10, from 10 to 5, from 5 to 3, from 3 to 2, from 2 to 1 or 1 amino acid residues are substituted, deleted or added, in any combination.

In a further aspect, the present invention provides polynucleotides that are RNA transcripts of the DNA sequences of the present invention. Accordingly, there is provided an RNA polynucleotide that:
(a) comprises an RNA transcript of the DNA sequence encoding the polypeptide of SEQ ID NO:2;
(b) is the RNA transcript of the DNA sequence encoding the polypeptide of SEQ ID NO:2;
(c) comprises an RNA transcript of the DNA sequence of SEQ ID NO:1; or
(d) is the RNA transcript of the DNA sequence of SEQ ID NO:1;
and RNA polynucleotides that are complementary thereto.

The polynucleotide sequence of SEQ ID NO:1 is a cDNA sequence that encodes the polypeptide of SEQ ID NO:2. The polynucleotide sequence encoding the polypeptide of SEQ ID NO:2 may be identical to the polypeptide encoding sequence of SEQ ID NO:1 or it may be a sequence other than SEQ ID NO:1, which, as a result of the redundancy (degeneracy) of the genetic code, also encodes the polypeptide of SEQ ID NO:2.

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one PHPIP-240 activity.

Polynucleotides of the present invention may be obtained using standard cloning and screening techniques from a cDNA library derived from mRNA in cells of heart, skeletal muscle, liver, kidney, brain. However PHP1 might as well be isolated from other human tissues, where lower levels are found. The substrate specificity identifies a role in the biosynthesis of fatty acids via preparation of acetylCoA. Accordingly, the biosynthesis of acetylcholine is regulated in nerve cells.

(see for instance, Sambrook et al., Molecular Cloning: A Laboratory Manual, 2nd Ed., Cold Spring Harbor Laboratory Press, Cold Spring Harbor, N.Y. (1989)). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself, or the coding sequence for the mature polypeptide in reading frame with other coding sequences, such as those encoding a leader or secretory sequence, a pre-, or pro- or prepro-protein sequence, or other fusion peptide portions. For example, a marker sequence that facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Polynucleotides that are identical, or have sufficient identity to a polynucleotide sequence of SEQ ID NO:1, may be used as hybridization probes for cDNA and genomic DNA or as primers for a nucleic acid amplification reaction (for instance, PCR). Such probes and primers may be used to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1, typically at least 95% identity. Preferred probes and primers will generally comprise at least 15 nucleotides, preferably, at least 30 nucleotides and may have at least 50, if not at least 100 nucleotides. Particularly preferred probes will have between 30 and 50 nucleotides. Particularly preferred primers will have between 20 and 25 nucleotides.

A polynucleotide encoding a polypeptide of the present invention, including homologs from species other than human, may be obtained by a process comprising the steps of screening a library under stringent hybridization conditions with a labeled probe having the sequence of SEQ ID NO: 1 or a fragment thereof, preferably of at least 15 nucleotides; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 microgram/ml denatured, sheared salmon sperm DNA; followed by washing the filters in 0.1×SSC at about 65° C. Thus the present invention also includes isolated polynucleotides, preferably with a nucleotide sequence of at least 100, obtained by screening a library under stringent hybridization conditions with a labeled probe having the sequence of SEQ ID NO:1 or a fragment thereof, preferably of at least 15 nucleotides.

The skilled artisan will appreciate that, in many cases, an isolated cDNA sequence will be incomplete, in that the region coding for the polypeptide does not extend all the way through to the 5' terminus. This is a consequence of reverse transcriptase, an enzyme with inherently low "processivity" (a measure of the ability of the enzyme to remain attached to the template during the polymerisation reaction), failing to complete a DNA copy of the mRNA template during first strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., Proc Nat Acad Sci USA 85, 8998–9002, 1988). Recent modifications of the technique, exemplified by the Marathon (trade mark) technology (Clontech Laboratories Inc.) for example, have significantly simplified the search for longer cDNAs. In the Marathon (trade mark) technology, cDNAs have been prepared from mRNA extracted from a chosen tissue and an 'adaptor' sequence ligated onto each end. Nucleic acid amplification (PCR) is then carried out to amplify the "missing" 5' end of the cDNA using a combination of gene specific and adaptor specific oligonucleotide primers. The PCR reaction is then repeated using 'nested' primers, that is, primers designed to anneal within the amplified product (typically an adapter specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems comprising a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Polynucleotides may be introduced into host cells by methods described in many standard laboratory manuals, such as Davis et al., Basic Methods in Molecular Biology (1986) and Sambrook et al. (ibid). Preferred methods of introducing polynucleotides into host cells include, for instance, calcium phosphate transfection, DEAE-dextran mediated transfection, transvection, micro-injection, cationic lipid-mediated transfection, electroporation, transduction, scrape loading, ballistic introduction or infection.

Representative examples of appropriate hosts include bacterial cells, such as *Streptococci, Staphylococci, E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector that is able to maintain, propagate or express a polynucleotide to produce a polypeptide in a host may be used. The appropriate polynucleotide sequence may be inserted into an expression system by any of a variety of well-known and routine techniques, such as, for example, those set forth in Sambrook et al., (ibid). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during intracellular synthesis, isolation and/or purification.

Polynucleotides of the present invention may be used as diagnostic reagents, through detecting mutations in the associated gene. Detection of a mutated form of the gene characterized by the polynucleotide of SEQ ID NO:1 in the cDNA or genomic sequence and which is associated with a dysfunction will provide a diagnostic tool that can add to, or define, a diagnosis of a disease, or susceptibility to a disease, which results from under-expression, overexpression or altered spatial or temporal expression of the gene. Individuals carrying mutations in the gene may be detected at the DNA level by a variety of techniques well known in the art.

Nucleic acids for diagnosis may be obtained from a subject's cells, such as from blood, urine, saliva, tissue biopsy or autopsy material. The genomic DNA may be used directly for detection or it may be amplified enzymatically by using PCR, preferably RT-PCR, or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled PHPIP-240 nucleotide sequences. Perfectly matched sequences can be distinguished from mismatched duplexes by RNase digestion or by differences in melting temperatures. DNA sequence difference may also be detected by alterations in the electrophoretic mobility of DNA fragments in gels, with or without denaturing agents, or by direct DNA sequencing (see, for instance, Myers et al., Science (1985) 230:1242).

Sequence changes at specific locations may also be revealed by nuclease protection assays, such as RNase and S1 protection or the chemical cleavage method (see Cotton et al., Proc Natl Acad Sci USA (1985) 85: 4397–4401).

An array of oligonucleotides probes comprising PHPIP-240 polynucleotide sequence or fragments thereof can be constructed to conduct efficient screening of e.g., genetic mutations. Such arrays are preferably high density arrays or grids. Array technology methods are well known and have general applicability and can be used to address a variety of questions in molecular genetics including gene expression, genetic linkage, and genetic variability, see, for example, M. Chee et al., Science, 274, 610–613 (1996) and other references cited therein.

Detection of abnormally decreased or increased levels of polypeptide or mRNA expression may also be used for diagnosing or determining susceptibility of a subject to a disease of the invention. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radio-immunoassays, competitive-binding assays, Western Blot analysis and ELISA assays.

Thus in another aspect, the present invention relates to a diagnostic kit comprising:

(a) a polynucleotide of the present invention, preferably the nucleotide sequence of SEQ ID NO: 1, or a fragment or an RNA transcript thereof;
(b) a nucleotide sequence complementary to that of (a);
(c) a polypeptide of the present invention, preferably the polypeptide of SEQ ID NO:2 or a fragment thereof; or
(d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or susceptibility to a disease, particularly diseases of the invention, amongst others.

The polynucleotide sequences of the present invention are valuable for chromosome localisation studies. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (co-inheritance of physically adjacent genes). Precise human chromosomal localisations for a genomic sequence (gene fragment etc.) can be determined using Radiation Hybrid (RH) Mapping (Walter, M. Spillett, D., Thomas, P., Weissenbach, J., and Goodfellow, P., (1994) A method for constructing radiation hybrid maps of whole genomes, Nature Genetics 7, 22–28). A number of RH panels are available from Research Genetics (Huntsville, Ala., USA) e.g. the GeneBridge4 RH panel (Hum Mol Genet 1996 March;5(3): 339–46 A radiation hybrid map of the human genome. Gyapay G, Schmitt K, Fizames C, Jones H, Vega-Czarny N, Spillett D, Muselet D, Prud'Homme JF, Dib C, Auffray C, Morissette J, Weissenbach J, Goodfellow PN). To determine the chromosomal location of a gene using this panel, 93 PCRs are performed using primers designed from the gene of interest on RH DNAs. Each of these DNAs contains random human genomic fragments maintained in a hamster background (human/hamster hybrid cell lines). These PCRs result in 93 scores indicating the presence or absence of the PCR product of the gene of interest. These scores are compared with scores created using PCR products from genomic sequences of known location. This comparison is conducted at http://www.genome.wi.mit.edu/. The gene of the present invention maps to human chromosome 13q33-q34 (D13S159-D13S280).

The polynucleotide sequences of the present invention are also valuable tools for issue expression studies. Such studies allow the determination of expression patterns of polynucleotides of the present invention which may give an indication as to the expression patterns of the encoded polypeptides in tissues, by detecting the mRNAs that encode them. The techniques used are well known in the art and include in situ hybridization techniques to clones arrayed on a grid, such as cDNA microarray hybridization (Schena et al, Science, 270, 467–470, 1995 and Shalon et al, Genome Res, 6, 639–45, 1996) and nucleotide amplification techniques such as PCR. A preferred method uses the TAQMAN (Trade mark) technology available from Perkin Elmer. Results from these studies can provide an indication of the normal function of the polypeptide in the organism. In addition, comparative studies of the normal expression pattern of mRNAs with that of mRNAs encoded by an alternative form of the same gene (for example, one having an alteration in polypeptide coding potential or a regulatory mutation) can provide valuable insights into the role of the polypeptides of the present invention, or that of inappropriate expression thereof in disease. Such inappropriate expression may be of a temporal, spatial or simply quantitative nature.

The polypeptides of the present invention are expressed in tissues of the heart, skeletal muscle, liver, kidney and brain.

A further aspect of the present invention relates to antibodies. The polypeptides of the invention or their fragments, or cells expressing them, can be used as immunogens to produce antibodies that are immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256: 495–497), the trioma technique, the human B-cell hybridoma technique (Kozbor et al., Immunology Today (1983) 4:72) and the EBV-hybridoma technique (Cole et al., Monoclonal Antibodies and Cancer Therapy, 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography. Antibodies against polypeptides of the present invention may also be employed to treat diseases of the invention, amongst others.

Polypeptides and polynucleotides of the present invention may also be used as vaccines. Accordingly, in a further aspect, the present invention relates to a method for inducing an immunological response in a mammal that comprises inoculating the mammal with a polypeptide of the present invention, adequate to produce antibody and/or T cell immune response, including, for example, cytokine-producing T cells or cytotoxic T cells, to protect said animal from disease, whether that disease is already established within the individual or not. An immunological response in a mammal may also be induced by a method comprises delivering a polypeptide of the present invention via a vector directing expression of the polynucleotide and coding for the polypeptide in vivo in order to induce such an immunological response to produce antibody to protect said animal from diseases of the invention. One way of administering the vector is by accelerating it into the desired cells as a coating on particles or otherwise. Such nucleic acid vector may comprise DNA, RNA, a modified nucleic acid, or a DNA/RNA hybrid. For use a vaccine, a polypeptide or a nucleic acid vector will be normally provided as a vaccine formulation (composition). The formulation may further comprise a suitable carrier. Since a polypeptide may be broken down in the stomach, it is preferably administered parenterally (for instance, subcutaneous, intra-muscular, intravenous, or intra-dermal injection). Formulations suitable for parenteral administration include aqueous and non-aqueous sterile injection solutions that may contain antioxidants, buffers, bacteriostats and solutes that render the formulation instonic with the blood of the recipient; and aqueous and non-aqueous sterile suspensions that may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine arid can be readily determined by routine experimentation.

Polypeptides of the present invention have one or more biological functions that are of relevance in one or more disease states, in particular the diseases of the invention hereinbefore mentioned. It is therefore useful to identify compounds that stimulate or inhibit the function or level of the polypeptide. Accordingly, in a further aspect, the present invention provides for a method of screening compounds to identify those that stimulate or inhibit the function or level of the polypeptide. Such methods identify agonists or antagonists that may be employed for therapeutic and prophylactic purposes for such diseases of the invention as hereinbefore mentioned. Compounds may be identified from a variety of sources, for example, cells, cell-free preparations, chemical libraries, collections of chemical compounds, and natural product mixtures. Such agonists or antagonists so-identified may be natural or modified substrates, ligands, receptors, enzymes, etc., as the case may be, of the polypeptide; a structural or functional mimetic thereof (see Coligan et al., Current Protocols in Immunology 1(2): Chapter 5 (1991)) or a small molecule. Such small molecules preferably have a molecular weight below 2,000 daltons, more preferably between 300 and 1,000 daltons, and most preferably between 400 and 700 daltons. It is preferred that these small molecules are organic molecules.

The screening method may simply measure the binding of a candidate compound to the polypeptide, or to cells or membranes bearing the polypeptide, or a fusion protein thereof, by means of a label directly or indirectly associated with the candidate compound. Alternatively, the screening method may involve measuring or detecting (qualitatively or quantitatively) the competitive binding of a candidate compound to the polypeptide against a labeled competitor (e.g. agonist or antagonist). Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Further, the screening methods may simply comprise the steps of mixing a candidate compound with a solution containing a polypeptide of the present invention, to form a mixture, measuring a PHPIP-240 activity in the mixture, and comparing the PHPIP240 activity of the mixture to a control mixture which contains no candidate compound.

Polypeptides of the present invention may be employed in conventional low capacity screening methods and also in high-throughput screening (HTS) formats. Such HTS formats include not only the well-established use of 96- and, more recently, 384-well micotiter plates but also emerging methods such as the nanowell method described by Schullek et al, Anal Biochem., 246, 20–29, (1997).

Fusion proteins, such as those made from Fc portion and PHPIP-240 polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)).

Screening Techniques

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents that may inhibit or enhance the production of polypeptide (also called antagonist or agonist, respectively) from suitably manipulated cells or tissues.

A polypeptide of the present invention may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide that compete with the binding of the polypeptide to its receptors, if any. Standard methods for conducting such assays are well understood in the art.

Examples of antagonists of polypeptides of the present invention include antibodies or, in some cases, oligonucleotides or proteins that are closely related to the ligands, substrates, receptors, enzymes, etc., as the case may be, of the polypeptide, e.g., a fragment of the ligands, substrates, receptors, enzymes, etc.; or a small molecule that bind to the polypeptide of the present invention but do not elicit a response, so that the activity of the polypeptide is prevented.

Screening methods may also involve the use of transgenic technology and PHPIP-240 gene. The art of constructing transgenic animals is well established. For example, the PHPIP-240 gene may be introduced through microinjection into the male pronucleus of fertilized oocytes, retroviral transfer into pre- or post-implantation embryos, or injection of genetically modified, such as by electroporation, embryonic stem cells into host blastocysts. Particularly useful transgenic animals are so-called "knock-in" animals in which an animal gene is replaced by the human equivalent within the genome of that animal. Knock-in transgenic animals are useful in the drug discovery process, for target validation, where the compound is specific for the human target. Other useful transgenic animals are so-called "knock-out" animals in which the expression of the animal ortholog of a polypeptide of the present invention and encoded by an endogenous DNA sequence in a cell is partially or completely annulled. The gene knock-out may be targeted to specific cells or tissues, may occur only in certain cells or tissues as a consequence of the limitations of the technology, or may occur in all, or substantially all, cells in the animal. Transgenic animal technology also offers a whole animal expression-cloning system in which introduced genes are expressed to give large amounts of polypeptides of the present invention Screening kits for use in the above described methods form a further aspect of the present invention. Such screening kits comprise:

(a) a polypeptide of the present invention;
(b) a recombinant cell expressing a polypeptide of the present invention;
(c) a cell membrane expressing a polypeptide of the present invention; or
(d) an antibody to a polypeptide of the present invention; which polypeptide is preferably that of SEQ ID NO:2.

It will be appreciated that in any such kit, (a), (b), (c) or (d) may comprise a substantial component.

Glossary

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is. "isolated" even if it is still present in said organism, which organism may be living or non-living.

"Polynucleotide" generally refers to any polyribonucleotide (RNA) or polydeoxribonucleotide (DNA), which may be unmodified or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any polypeptide comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques that are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, Proteins—Structure and Molecular Properties, 2nd Ed., T. E. Creighton, W. H. Freeman and Company, New York, 1993; Wold, F., Post-translational Protein Modifications: Perspectives and Prospects, 1–12, in Post-translational Covalent Modification of Proteins, B. C. Johnson, Ed., Academic Press, New York, 1983; Seifter et al., "Analysis for protein modifications and nonprotein cofactors", Meth Enzymol, 182, 626–646, 1990, and Rattan et al., "Protein Synthesis: Post-translational Modifications and Aging", Ann NY Acad Sci, 663, 48–62, 1992).

"Fragment" of a polypeptide sequence refers to a polypeptide sequence that is shorter than the reference sequence but that retains essentially the same biological function or activity as the reference polypeptide. "Fragment" of a polynucleotide sequence refers to a polynucleotide sequence that is shorter than the reference sequence of SEQ ID NO:1.

"Variant" refers to a polynucleotide or polypeptide that differs from a reference polynucleotide or polypeptide, but retains the essential properties thereof. A typical variant of a polynucleotide differs in nucleotide sequence from the reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from the reference polypeptide. Generally, alterations are limited so that the sequences of the reference polypeptide and the variant are closely similar overall and, in many regions, identical. A variant and reference polypeptide may differ in amino acid sequence by one or more substitutions, insertions, deletions in any combination. A substituted or inserted amino acid residue may or may not be one encoded by the genetic code. Typical conservative substitutions include Gly, Ala; Val, Ile, Leu; Asp, Glu; Asn, Gin; Ser, Thr; Lys, Arg; and Phe and Tyr. A variant of a polynucleotide or polypeptide may be naturally occurring such as an allele, or it may be a variant that is not known to occur naturally. Non-naturally occurring variants of polynucleotides and polypeptides may be made by mutagenesis techniques or by direct synthesis. Also included as variants are polypeptides having one or more post-translational modifications, for instance glycosylation, phosphorylation, methylation, ADP ribosylation and the like. Embodiments include methylation of the N-terminal amino acid, phosphorylations of serines and threonines and modification of C-terminal glycines.

"Allele" refers to one of two or more alternative forms of a gene occurring at a given locus in the genome.

"Polymorphism" refers to a variation in nucleotide sequence (and encoded polypeptide sequence, if relevant) at a given position in the genome within a population.

"Single Nucleotide Polymorphism" (SNP) refers to the occurrence of nucleotide variability at a single nucleotide position in the genome, within a population. An SNP may occur within a gene or within intergenic regions of the genome. SNPs can be assayed using Allele Specific Amplification (ASA). For the process at least 3 primers are required. A common primer is used in reverse complement to the polymorphism being assayed. This common primer can be between 50 and 1500 bps from the polymorphic base. The other two (or more) primers are identical to each other except that the final 3' base wobbles to match one of the two (or more) alleles that make up the polymorphism. Two (or more) PCR reactions are then conducted on sample DNA, each using the common primer and one of the Allele Specific Primers.

"Splice Variant" as used herein refers to cDNA molecules produced from RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule each of that may encode different amino acid sequences. The term splice variant also refers to the proteins encoded by the above cDNA molecules.

"Identity" reflects a relationship between two or more polypeptide sequences or two or more polynucleotide sequences, determined by comparing the sequences. In general, identity refers to an exact nucleotide to nucleotide or amino acid to amino acid correspondence of the two polynucleotide or two polypeptide sequences, respectively, over the length of the sequences being compared.

"% Identity"—For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

"Similarity" is a further, more sophisticated measure of the relationship between two polypeptide sequences. In general, "similarity" means a comparison between the amino acids of two polypeptide chains, on a residue by residue basis, taking into account not only exact correspondences between a between pairs of residues, one from each of the sequences being compared (as for identity) but also, where there is not an exact correspondence, whether, on an evolutionary basis, one residue is a likely substitute for the other. This likelihood has an associated "score" from which the "% similarity" of the two sequences can then be determined.

Methods for comparing the identity and similarity of two or more sequences are well known in the art. Thus for instance, programs available in the Wisconsin Sequence Analysis Package, version 9.1 (Devereux J et al, Nucleic Acids Res, 12, 387–395, 1984, available from Genetics Computer Group, Madison, Wis., USA), for example the programs BESTFIT and GAP, may be used to determine the % identity between two polynucleotides and the % identity and the % similarity between two polypeptide sequences. BESTFIT uses the "local homology" algorithm of Smith and Waterman (J Mol Biol, 147,195–197, 1981, Advances in Applied Mathematics, 2, 482–489, 1981) and finds the best single region of similarity between two sequences. BESTFIT is more suited to comparing two polynucleotide or two polypeptide sequences that are dissimilar in length, the program assuming that the shorter sequence represents a portion of the longer. In comparison, GAP aligns two sequences, finding a "maximum similarity", according to the algorithm of Neddleman and Wunsch (J Mol Biol, 48, 443–453, 1970). GAP is more suited to comparing sequences that are approximately the same length and an alignment is expected over the entire length. Preferably, the parameters "Gap Weight" and "Length Weight" used in each program are 50 and 3, for polynucleotide sequences and 12 and 4 for polypeptide sequences, respectively. Preferably, % identities and similarities are determined when the two sequences being compared are optimally aligned.

Other programs for determining identity and/or similarity between sequences are also known in the art, for instance the BLAST family of programs (Altschul S F et al, J Mol Biol, 215, 403–410, 1990, Altschul S F et al, Nucleic Acids Res., 25:389–3402, 1997, available from the National Center for Biotechnology Information (NCBI), Bethesda, Md., USA and accessible through the home page of the NCBI at www.ncbi.nlm.nih.gov) and FASTA (Pearson W R, Methods in Enzymology, 183, 63–99, 1990; Pearson W R and Lipman D J, Proc Nat Acad Sci USA, 85, 2444–2448,1988, available as part of the Wisconsin Sequence Analysis Package).

Preferably, the BLOSUM62 amino acid substitution matrix (Henikoff S and Henikoff J G, Proc. Nat. Acad. Sci. USA, 89, 10915–10919, 1992) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a reference polynucleotide or a polypeptide sequence, the query and the reference sequence being optimally aligned and the parameters of the program set at the default value, as hereinbefore described.

"Identity Index" is a measure of sequence relatedness which may be used to compare a candidate sequence (polynucleotide or polypeptide) and a reference sequence. Thus, for instance, a candidate polynucleotide sequence having, for example, an Identity Index of 0.95 compared to a reference polynucleotide sequence is identical to the reference sequence except that the candidate polynucleotide sequence may include on average up to five differences per each 100 nucleotides of the reference sequence. Such differences are selected from the group consisting of at least one nucleotide deletion, substitution, including transition and transversion, or insertion. These differences may occur at the 5' or 3' terminal positions of the reference polynucleotide sequence or anywhere between these terminal positions, interspersed either individually among the nucleotides in the reference sequence or in one or more contiguous groups within the reference sequence. In other words, to obtain a polynucleotide sequence having an Identity Index of 0.95 compared to a reference polynucleotide sequence, an average of up to 5 in every 100 of the nucleotides of the in the reference sequence may be deleted, substituted or inserted, or any combination thereof, as hereinbefore described. The same applies mutatis mutandis for other values of the Identity Index, for instance 0.96, 0.97, 0.98 and 0.99.

Similarly, for a polypeptide, a candidate polypeptide sequence having, for example, an Identity Index of 0.95 compared to a reference polypeptide sequence is identical to the reference sequence except that the polypeptide sequence may include an average of up to five differences per each 100 amino acids of the reference sequence. Such differences are selected from the group consisting of at least one amino acid deletion, substitution, including conservative and non-conservative substitution, or insertion. These differences may occur at the amino- or carboxy-terminal positions of the reference polypeptide sequence or anywhere between these terminal positions, interspersed either individually among the amino acids in the reference sequence or in one or more contiguous groups within the reference sequence. In other words, to obtain a polypeptide sequence having an Identity Index of 0.95 compared to a reference polypeptide sequence, an average of up to 5 in every 100 of the amino acids in the reference sequence may be deleted, substituted or inserted, or any combination thereof, as hereinbefore described. The same applies mutatis mutandis for other values of the Identity Index, for instance 0.96, 0.97, 0.98 and 0.99.

The relationship between the number of nucleotide or amino acid differences and the Identity Index may be expressed in the following equation:

$$n_a \leq x_a - (x_a \cdot I)$$

in which:

$n_a$ is the number of nucleotide or amino acid differences, $x_a$ is the total number of nucleotides or amino acids in SEQ ID NO:1 or SEQ ID NO:2, respectively, I is the Identity Index, · is the symbol for the multiplication operator, and in which any non-integer product of $X_a$ and I is rounded down to the nearest integer prior to subtracting it from $x_a$.

"Homolog" is a generic term used in the art to indicate a polynucleotide or polypeptide sequence possessing a high degree of sequence relatedness to a reference sequence. Such relatedness may be quantified by determining the degree of identity and/or similarity between the two sequences as hereinbefore defined. Falling within this generic term are the terms "ortholog", and "paralog". "Ortholog" refers to a polynucleotide or polypeptide that is the functional equivalent of the polynucleotide or polypeptide in another species. "Paralog" refers to a polynucleotide or polypeptide that within the same species which is functionally similar.

"Fusion protein" refers to a protein encoded by two, unrelated, fused genes or fragments thereof. Examples have been disclosed in U.S. Pat. Nos. 5,541,087, 5,726,044. In the case of Fc-PHPIP-240, employing an immunoglobulin Fc region as a part of a fusion protein is advantageous for performing the functional expression of Fc-PHPIP-240 or fragments of PHPIP-240, to improve pharmacokinetic properties of such a fusion protein when used for therapy and to generate a dimeric PHPIP-240. The Fc-PHPIP-240 DNA construct comprises in 5' to 3' direction, a secretion cassette, i.e. a signal sequence that triggers export from a mammalian cell, DNA encoding an immunoglobulin Fc region fragment, as a fusion partner, and a DNA encoding PHPIP-240 or fragments thereof. In some uses it would be desirable to be able to alter the intrinsic functional properties (complement binding, Fc-Receptor binding) by mutating the functional Fc sides while leaving the rest of the fusion protein untouched or delete the Fc part completely after expression.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

FURTHER EXAMPLES

Plasmid Constructs (All Plasmids were Verified by Sequencing)

Cloning of pDBLeu—PHPI

The cDNA encoding PHP1 was amplified by PCR using the primers HispaseSal-up (SEQ ID NO: 3, primer 1) and Hispase-Not-low (SEQ ID NO: 4, primer 2) and ligated into vector pCR2.1TOPO (Invitrogen). Subsequently, the vector was cleaved using Sal1 and Not1 and the PHP1-encoding fragment was ligated into pDBLeu.

Cloning of pLexA-MCS—PHPI

Oligonucleotide primer 3 Y2H-MCS1 (SEQ ID NO. 5) and primer 4 SEQ ID NO. 6 Y2H-MCS2 were annealed and ligated into EcoR1 and Sal1 restingated vector pLexA (Clontech) to generate Vector pLexA-MCS containing unique $EcoR_1$, Sal1, Xho1 and Not1 restriction sites.

A fragment encoding PHP1 was isolated from Vector pDBLeu-PHP1 using Not1 and Sal1 and ligated into Vector pLexA-MCS to generate pLexA-MCSPHP1. All vectors were confirmed by sequencing.

Fusionproteins

The peptide sequence of the Gal4-PHP1 fusion protein is given in SEQ ID NO: 7 comprising the Gal4 protein and a C-terminally linked full length PHP-1 protein. The corresponding peptide sequence of the LexA-PHP-1 fusion protein comprised the LexA protein sequence and a C-terminally linked full length PHP-1 protein. The sequence has been disclosed in SEQ ID NO: 8.

Yeast-Two Hybrid Screen to select PHP1-Interacting Proteins.

The yeast two-hybrid screening method is technically simple and very rapid such that several million of library clones can be screened in just a few days. All of the elements of the system are commercially available. In the screen, the His3 indicator gene will only be activated if the DNA binding domain of Gal4 (AA 1–147) and the Gal4 transactivation domain (AA 768–881) fused to the NLS of the SV40 large T antigen are brought into contact by the receptor Histidine Phosphatase and a protein ligand interaction. Although the ligands isolated from this screen bind to Histidine Phosphatase the binding partners have been confirmed in a second different—LexA-based Yeast-Two Hybrid selection scheme. If both screening procedures are implemented concurrently, ligands obtained may be tested in other systems.

A yeast Two Hybrid screen (Proquest, Life Technologies) using pDBLeuPHP1 as bait construct and a HELA-based cDNA library as prey was performed as described (selection was performed on -Trp, -Leu, -His Minimalmedium containing 25 mM 3-Aminotriazole). Interaction was confirmed on Medium lacking Uracile, Tryptophane and Leucine as described in the manufacturers protocoll.

One positive clone representing a PHPIP-240—gene product was isolated and sequenced.

Confirmation of the PHPIP-240 ligand interaction using a LexA-based Yeast-Two Hybrid selection scheme:

To confirm the interaction in a different selection scheme, the Matchmaker LexA Two-Hybrid system (Clontech) was used due to manufacturers conditions. Vector pLexA-MCS-PHP1 was used as bait. Vector pPC86-PHPIP240, which was isolated in the Gal4 based Yeast Two Hybrid system as described above was used as prey.

Interaction of p53 and large T antigen were used as positve controls in *S. cerevisiae* strain EGY48-pSH18–32.

In Silico Analysis

The gene for the PHP1 ligand identified in above mentioned yeast-two-hybrid screen is located on chromosome 13q33-q34 (D13S159-D13S280). The identified gene encodes a protein of 1047 AA length, with no significant sequence homology to other known proteins. While partial sequences of this gene and their corresponding virtual ORF predictions have already been deposited in the databank a protein function as revealed in this study has not been described previously.

The invention claimed is:

1. An isolated and purified protein histidine phosphatase interacting partner of 240kd (PHPIP-240) polypeptide selected from the group consisting of:
   (a) a polypeptide encoded by a polynucleotide comprising the sequence of SEQ ID NO:1;
   (b) a polypeptide comprising the polypeptide sequence of SEQ ID NO:2;
   (c) the polypeptide sequence of SEQ ID NO:2,
   wherein said PHPIP-240 of (a) to (c) has the ability to bind specifically to the protein histidine phosphatase 1 (PHPI) having the amino acid sequence shown in SEQ ID NO: 9.

2. The polypeptide of claim 1 comprising the polypeptide sequence of SEQ ID NO:2.

3. The polypeptide of claim 1 consisting of the polypeptide sequence of SEQ ID NO:2.

4. A polypettide of claim 1, further comprising an Immunoglobulin Fc-region.

* * * * *